(12) United States Patent
Burgess

(10) Patent No.: US 11,450,417 B2
(45) Date of Patent: Sep. 20, 2022

(54) SYSTEM AND METHOD FOR HEALTHCARE DOCUMENT MANAGEMENT

(71) Applicant: RexPay, Inc., Phoenix, AZ (US)

(72) Inventor: Harlow Burgess, Chandler, AZ (US)

(73) Assignee: Rivia Health Inc., Phoenix, AZ (US)

( * ) Notice: Subject to any disclaimer, the term of this patent is extended or adjusted under 35 U.S.C. 154(b) by 410 days.

(21) Appl. No.: 16/775,064

(22) Filed: Jan. 28, 2020

(65) Prior Publication Data

US 2020/0243174 A1    Jul. 30, 2020

Related U.S. Application Data

(60) Provisional application No. 62/797,710, filed on Jan. 28, 2019.

(51) Int. Cl.
| | |
|---|---|
| *G16H 10/60* | (2018.01) |
| *G06K 9/00* | (2022.01) |
| *G06F 16/242* | (2019.01) |
| *G06F 16/22* | (2019.01) |
| *G06F 16/93* | (2019.01) |
| *G06N 20/00* | (2019.01) |
| *G06F 40/279* | (2020.01) |
| *G06K 9/62* | (2022.01) |
| *G06V 30/412* | (2022.01) |
| *G06V 30/413* | (2022.01) |
| *G06V 30/414* | (2022.01) |

(Continued)

(52) U.S. Cl.
CPC .............. *G16H 10/60* (2018.01); *G06F 16/22* (2019.01); *G06F 16/243* (2019.01); *G06F 16/93* (2019.01); *G06F 40/279* (2020.01); *G06K 9/6262* (2013.01); *G06N 20/00* (2019.01); *G06V 30/412* (2022.01); *G06V 30/413* (2022.01); *G06V 30/414* (2022.01); *G06V 30/416* (2022.01); *G06V 30/10* (2022.01)

(58) Field of Classification Search
CPC ....... G16H 10/60; G06F 16/243; G06F 16/22; G06F 16/93; G06F 40/279; G06N 20/00; G06V 30/413; G06V 30/416; G06V 30/412; G06V 30/414; G06V 30/10; G06K 9/6262
See application file for complete search history.

(56) References Cited

U.S. PATENT DOCUMENTS

| | | | | |
|---|---|---|---|---|
| 2010/0241595 | A1* | 9/2010 | Felsher | G16H 10/65 707/E17.014 |
| 2013/0085781 | A1* | 4/2013 | Navani | G06Q 10/06 705/3 |

\* cited by examiner

*Primary Examiner* — Quang N Vo
(74) *Attorney, Agent, or Firm* — Rodney J. Fuller; Booth Udall Fuller, PLC

(57) ABSTRACT

A medical expense document management system including a document management server is disclosed. The server is configured to receive from a user client device an image of a medical document, convert the image into a plurality of text elements using OCR, and determine a source of the document. The server is also configured to retrieve data detectors from a database, each data detector associated with a data type anticipated to be in the document, each detector having at least one identifier, at least one direction describing a potential relative direction of a text element having a label associated with the detector, and at least one validation criteria. The server is also configured to identify a potential descriptor by comparing each text element with the at least one identifier, determine if the text element pointed to by one of the directions meets the validation criteria, and store the validated text element.

20 Claims, 8 Drawing Sheets

(51) Int. Cl.
*G06V 30/416* (2022.01)
*G06V 30/10* (2022.01)

SYSTEM AND METHOD FOR HEALTHCARE DOCUMENT MANAGEMENT

RELATED APPLICATIONS

This application claims the benefit of U.S. provisional patent application 62/797,710, filed Jan. 28, 2019 titled "System and Method for Medical Bill Management," the entirety of the disclosure of which is hereby incorporated by this reference.

TECHNICAL FIELD

Aspects of this document relate generally to healthcare document management.

BACKGROUND

Alongside new medical treatments and diagnostic technologies, modern medicine has spawned a complex ecosystem of service providers and insurers. It is not uncommon for an individual, in the wake of an event such as a car accident, to be receiving bills and other documents not only from their health insurance company, but also hospitals, doctors, specialists, ambulance companies, laboratories, pharmacies, and other parties. Each of these parties has their own timeline and procedure for payment, sometimes even using different terminology to describe the same thing. It is very easy for an individual to be overwhelmed by all of the moving parts that make up the system that is helping them get healthy.

Juggling the deadlines of multiple bills, making sure promised insurance benefits are being utilized fully, and ensuring no mistakes have been made, would be difficult under the best of circumstances, let alone while one is also recovering. Bills sometimes slip through the cracks or become too much to pay, resulting in accounts going to collections, to the detriment of both the individual and the entity seeking payment.

SUMMARY

According to one aspect, a healthcare document management system includes a document management server communicatively coupled to a database, and further communicatively coupled to a user client device through a network. The document management server is configured to create a user record associated with a user, using information received, at least in part, from the user client device, receive from the user client device an image of a medical document, and convert the image of the medical document into a plurality of text elements using optical character recognition, each text element having a content and an absolute position in the document. The server is also configured to determine if a document type of the medical document is one of a bill and an explanation of benefits by searching the content of each text element for at least one distinguishing string, each distinguishing string being unique to one document type. The server is configured to identify all postal addresses in the medical document by inspecting the content of each text element for a postal address format, validate each postal address, place each postal address in a standardized postal address format, and determine a source of the medical document by comparing each identified postal address with a list of postal addresses unique to known sources. The source is one of a healthcare provider and an insurer. The server is also configured to determine a source of the medical document having postal addresses not found on the list by examining text elements neighboring each postal address that does not match a postal address found on the user record, and retrieve a plurality of data detectors from the database based on the document type. Each data detector is associated with a data type that is anticipated to be in the document, each data detector having at least one identifier that is one of a potential label and a potential format, at least one direction describing a potential relative direction of a text element having a label associated with the data detector, and at least one validation criteria. Each validation criteria describes one of a valid format and a valid range. The server is configured to, for each data detector, order at least one of the identifiers and the directions according to a history stored in the database and associated with the source, identify a table within the document by calculating for each text element of the plurality of text elements a relative position of at least one neighboring text element relative to the text element using the absolute position of the text element, and comparing the relative positions of the plurality of text elements. The server is also configured to locate a header for the table by comparing the content of the text elements within the table with the identifiers of the plurality of data detectors and then identifying the data type of the matching text elements, the header being one of a row and a column. The server is configured to validate, for each identified text element in the header, at least one text element within the other of a row and a column described by the identified text element in the header with the validation criteria of the data detector that identified the identified text element in the header, and associate, for each identified text element in the header, at least one validated text element within the other of the row and the column described by the identified text element in the header with the data detector that identified the identified text element in the header. The server is configured to identify a potential descriptor by comparing the content of each text element not part of the table with the at least one identifier of at least one data detector, determine if the text element pointed to by one of the at least one direction of the data detector used to identify the potential descriptor meets the validation criteria of the data detector, associate the validated text element with the data detector, and send to the user client device, for each text element associated with one data detector of the plurality of data detector, the content of the text element, for verification from the user. The server is also configured to receive a verification message from the user client device, store the verified content in a first document record in the database, the first document record being linked to the user record, and compare the first document record with records associated with other medical documents linked to the user record. The server is configured to notify the user through the user client device that the medical document is a duplicate upon determination that the medical record already exists, pair the first document record, which describes one of an explanation of benefits and a bill, with a second document record which describes the other of an explanation of benefits and a bill, based upon at least a common date, and determine if there is a discrepancy between a patient responsibility according to the first document record and a patient responsibility according to the second document record. The server is configured to notify the user through the user client device of the discrepancy, generate and transmit a billing discrepancy notification to a healthcare provider who is the source of one of the bill associated with one of the first document record and the second document record, in response to receipt by the document management server of permission from the user client device, and generate a list of payments due by collecting payment details from each bill described by one of a plurality of document records linked to the user record. The server is configured do send the list to the user client device, and update, for each data detector, the history associated with the source, according to which identifier of the at least one identifier and which direction of the at least one direction matched the most text elements of the data type described by the data detector in the document.

Particular embodiments may comprise one or more of the following features. The document management server may be further configured to determine if the document type of the medical document is an insurance card through at least one of comparing a size of the text elements relative to a size of the medical document and searching the content of each text element for at least one distinguishing string unique to insurance cards. The server may be configured to retrieve a second plurality of data detectors from the database. Each data detector may be associated with a data type that is anticipated to be in the insurance card. The server may be configured to store the verified content in the user record if the document type is insurance card. The document management server may be further configured to receive, from the user client device, a query made by the user in natural language, parse the query, search the database for data associated to the parsed query, and/or send data associated to the parsed query to the user client device. The server may be configured to escalate the query to a human agent, in response to a lack of data associated to the parsed query in the database, by sending the query to an agent client communicatively coupled to the document management server. The data associated to the parsed query may be retrieved, in part, from the user record, and may be specific to the user. The document management server may be communicatively coupled to at least one of a healthcare provider server and an insurer server through the network. The document management server may be further configured to receive an external document record directly from one of the healthcare server and the insurer server.

According to another aspect of the disclosure, a healthcare document management system includes a document management server communicatively coupled to a database, and further communicatively coupled to a user client device through a network. The document management server is configured to create a user record associated with a user, using information received, at least in part, from the user client device, store the user record in the database, receive from the user client device an image of a medical document, and convert the image of the medical document into a plurality of text elements using optical character recognition. Each text element has a content and an absolute position in the document. The server is configured to identify all postal addresses in the medical document by inspecting the content of each text element for a postal address format, validate each postal address, place each postal address in a standardized postal address format, and determine a source of the medical document by comparing each identified postal address with a list of postal addresses unique to known sources. The source is one of a healthcare provider and an insurer. The server is configured to determine a source of the medical document having postal addresses not found on the list by examining text elements neighboring each postal address that does not match a postal address found on the user record, and retrieve a plurality of data detectors from the database, each data detector associated with a data type that is anticipated to be in the document, each data detector comprising at least one identifier that is one of a potential label and a potential format, at least one direction describing a potential relative direction of a text element having a label associated with the data detector, and at least one validation criteria. Each validation criteria describes one of a valid format and a valid range. The server is also configured to identify a potential descriptor by comparing the content of each text element with the at least one identifier of at least one data detector, determine if the text element pointed to by one of the at least one direction of the data detector used to identify the potential descriptor meets the validation criteria of the data detector, associate the validated text element with the data detector, and send to the user client device, for each text element associated with one data detector of the plurality of data detector, the content of the text element, for verification from the user. The server is configured to receive a verification message from the user client device, and store the verified content in a first document record in the database, the first document record being linked to the user record.

Particular embodiments may comprise one or more of the following features. The document management server may be further configured to compare the first document record with records associated with other medical documents linked to the user record, and/or notify the user through the user client device that the medical document is a duplicate upon determination that the medical record already exists. The document management server may be further configured to determine if a document type of the medical document is one of a bill and an explanation of benefits by searching the content of each text element for at least one distinguishing string. Each distinguishing string may be unique to one document type. The server may also be configured to pair the first document record, which may describe one of an explanation of benefits and a bill, with a second document record which may describe the other of an explanation of benefits and a bill, based upon at least a common date. Retrieving the plurality of data detectors from the database may be based, at least in part, on the document type. The document management server may be further configured to determine if there is a discrepancy between a patient responsibility according to the first document record and a patient responsibility according to the second document record, and/or notify the user through the user client device of the discrepancy. The document management server may be further configured to determine if the document type of the medical document is an insurance card through at least one of comparing a size of the text elements relative to a size of the medical document and searching the content of each text element for at least one distinguishing string unique to insurance cards, and/or retrieve a second plurality of data detectors from the database. Each data detector may be associated with a data type that is anticipated to be in the insurance card. The server may be configured to store the verified content in the user record if the document type is insurance card. The data associated to the parsed query may be retrieved, in part, from the user record, and may be specific to the user. The document management server may be further configured to, for each data detector, order at least one of the identifiers and the directions according to a history stored in the database and associated with the source, and/or update, for each data detector, the history associated with the source, according to which identifier of the at least one identifier and which direction of the at least one direction matched the most text elements of the data type described by the data detector in the document. The document management server may be further configured to identify a table within the document by calculating for each text element of the plurality of text elements a relative position of at least one neighboring text element relative to the text element using the absolute position of the text element, and comparing the relative positions of the plurality of text elements. The server may be configured to locate a header for the table by comparing the content of the text elements within the table with the identifiers of the plurality of data detectors and then identifying the data type of the matching text elements. The header may be one of a row and a column. The server may be configured to validate, for each identified text element in the header, at least one text element within the other of a row and a column described by the identified text element in the header with the validation criteria of the data detector that identified the identified text element in the header, and/or associate, for each identified text element in the header, at least one validated text element within the other of the row and the column described by the identified text element in the header with the data detector that identified the identified text element in the header. The document management server may be communicatively coupled to at least one of a healthcare provider server and an insurer server through the network. The document management server may be further configured to receive an external document record directly from one of the healthcare server and the insurer server.

According to yet another aspect of the disclosure, a computer-implemented method for healthcare document management includes creating, with a processor, a user record associated with a user, using information received, at least in part, from a user client device. The method also includes receiving, by the processor, from the user client device an image of a medical document, and converting, with the processor, the image of the medical document into a plurality of text elements using optical character recognition. Each text element has a content and an absolute position in the document. The method includes identifying, with the processor, all postal addresses in the medical document by inspecting the content of each text element for a postal address format, and determining, with the processor, a source of the medical document by comparing each identified postal address with a list of postal addresses unique to known sources. The source is one of a healthcare provider and an insurer. The method may also include determining, with the processor, a source of the medical document having postal addresses not found on the list by examining text elements neighboring each postal address that does not match a postal address found on the user record, and retrieving, with the processor, a plurality of data detectors, each data detector associated with a data type that is anticipated to be in the document. Each data detector includes at least one identifier that is one of a potential label and a potential format, at least one direction describing a potential relative direction of a text element having a label associated with the data detector, and at least one validation criteria. Each validation criteria describes one of a valid format and a valid range. The method includes identifying, with the processor, a potential descriptor by comparing the content of each text element with the at least one identifier of at least one data detector, and determining, with the processor, if the text element pointed to by one of the at least one direction of the data detector used to identify the potential descriptor meets the validation criteria of the data detector. The method further includes associating, in a memory, the validated text element with the data detector, and sending, with the processor, to the user client device, for each text element associated with one data detector of the plurality of data detector, the content of the text element, for verification from the user. The method includes receiving, by the processor, a verification message from the user client device, and storing, in the memory, the verified content in a first document record, the first document record being linked to the user record.

Particular embodiments may comprise one or more of the following features. The method may further include determining, with the processor, if a document type of the medical document is one of a bill and an explanation of benefits by searching the content of each text element for at least one distinguishing string. Each distinguishing string may be unique to one document type. The method may further include pairing, in the memory, the first document record, which describes one of an explanation of benefits and a bill, with a second document record which describes the other of an explanation of benefits and a bill, based upon at least a common date, determining if there is a discrepancy between a patient responsibility according to the first document record and a patient responsibility according to the second document record, and/or notifying the user through the user client device of the discrepancy. The method may further include determining if the document type of the medical document is an insurance card through at least one of comparing a size of the text elements relative to a size of the medical document and searching the content of each text element for at least one distinguishing string unique to insurance cards. The method may further include retrieving a second plurality of data detectors. Each data detector may be associated with a data type that is anticipated to be in the insurance card. The method may further include storing the verified content in the user record if the document type is insurance card. The method may include comparing, with the processor, the first document record with records associated with other medical documents linked to the user record, and/or notifying, with the processor, the user through the user client device that the medical document is a duplicate upon determination that the medical record already exists. The method may include, for each data detector, ordering at least one of the identifiers and the directions according to a history associated with the source, and/or updating, for each data detector, the history associated with the source, according to which identifier of the at least one identifier and which direction of the at least one direction matched the most text elements of the data type described by the data detector in the document. The method may further include training a machine learning model correlating text elements with the data detectors with which they have been associated, and/or determining whether the machine learning model performs better than one or more data detectors. The method may include automatically employing the machine learning model in place of the one or more data detectors once the machine learning model outperforms the one or more data detectors.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

Figure 1:
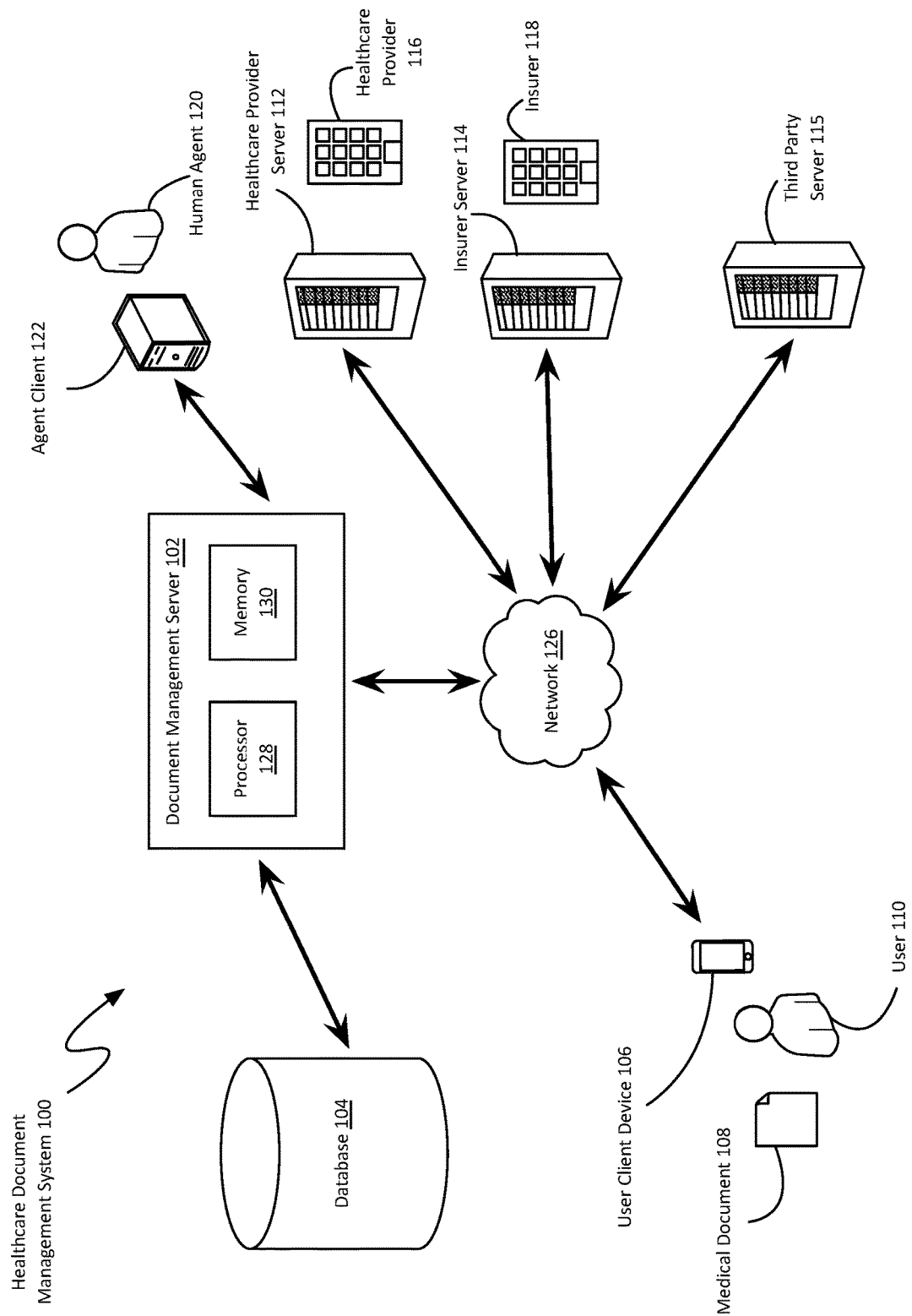
FIG. 1 is a network view of a healthcare document management system.

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

Alongside new medical treatments and diagnostic technologies, modern medicine has spawned a complex ecosystem of service providers and insurers. It is not uncommon for an individual, in the wake of an event such as a car accident, to be receiving bills and other documents not only from their health insurance company, but also hospitals, doctors, specialists, ambulance companies, laboratories, pharmacies, and other parties. Each of these parties has their own timeline and procedure for payment, sometimes even using different terminology to describe the same thing. It is very easy for an individual to be overwhelmed by all of the moving parts that make up the system that is helping them get healthy.

Juggling the deadlines of multiple bills, making sure promised insurance benefits are being utilized fully, and ensuring no mistakes have been made, would be difficult under the best of circumstances, let alone while one is also recovering. Bills sometimes slip through the cracks or become too much to pay, resulting in accounts going to collections, to the detriment of both the individual and the entity seeking payment.

Contemplated herein is a system and method for healthcare document management for patients. This healthcare document management system allows a user to organize and track all of their bills, insurance documents, and payments, across numerous providers and insurers. The system streamlines and clarifies a sometimes intimidating and overwhelming process, allowing the user to focus on their health and recovery. Additionally, some embodiments assist the user in reducing their medical expenses, whether by identifying billing errors, recognizing opportunities for less expensive options, or identifying financial assistance the user qualifies for.

In addition to being beneficial to the end user (i.e. the patient), the systems and methods disclosed herein are also beneficial to the healthcare providers and insurance companies. Helping the patient keep track of billing deadlines and making them aware of payment options or financing means the providers are more likely to be paid, and paid sooner. The clarification regarding the services provided, their cost, and their coverage may help reduce inquiry churn experienced by the insurance company. Additionally, some embodiments may also help detect billing errors that otherwise may go undetected. These systems may also benefit employers, making provided benefits more useful to their employees, at a reduced cost to the employer.

Advantageously, this system may integrate with the systems and procedures commonly used by providers and insurers. For example, some embodiments are configured such that a user can scan in bills, explanations of benefits, and other documents simply by taking a photo of a hard copy with a mobile device or forwarding an email containing a digital copy. Some embodiments of the system and method disclosed herein are capable of automatically ingesting these documents, without knowing their origin or how they are formatted. Conventional systems must rely on either manual entry of these documents, or fragile automated systems that must be manually taught every new document format. The automatic ingestion of documents contemplated herein allows this system to benefit all parties involved in the healthcare of the patient, without placing much of a burden on any single party.

FIG. 1 is a network view of a non-limiting example of a healthcare document management system 100. As shown, the system 100 comprises a document management server 102 communicatively coupled to a user client device 106 through a network 126. The document management server 102 is also communicatively coupled to a database 104.

Going forward, reference is made to a user 110 of the system 100. In the context of the present description and the claims that follow, a user 110 is an individual interfacing or interacting with the system 100 on behalf of a recipient of medical services. A user 110 may or may not also be a patient. For example, in some embodiments, the system 100 may be used to manage the documents and benefits for a family, meaning the user 110 may be a parent organizing the bills associated with the treatment of their child, the patient.

Furthermore, the following discussion will be carried out in the context of medical bills and medical insurance. However, this should not be construed as a limitation. It should be noted that the systems and methods contemplated herein could also be applied to other types of services/bills/insurance including, but not limited to, vision, dental, and pharmaceutical, and that such application could be performed either instead of, or along side, application to medical treatments/insurance, and the like.

As shown, the system 100 includes a document management server 102 having a processor 128 and a memory 130. The server 102 is responsible for collecting the medical documents 108 (e.g. bills, explanation of benefits, etc.) and other information related to a user 110, organizing said information to make it clear which party (e.g. doctor, hospital, imaging center, pharmacy, insurer, etc.) did/paid what, and when. According to some embodiments, the server 102 may assist the user in keeping track of remaining benefits and debts, making payments on time, and finding ways to save money.

In some embodiments, the server 102 may be a discrete piece of hardware, while in others it may be a distributed computing environment spread across multiple machines. In some embodiments, the server 102 may be localized to one of the entities associated with the user's treatment (e.g. hospital, insurance company, employer, etc.), while in others the server 102 may be hosted and maintained by a separate entity. In some embodiments, the server 102 may be implemented in a cloud environment (e.g. the functionality described may be provided in an instantiated environment implemented on remote hardware, etc.).

In some embodiments, a server 102 may provide the functionality disclosed herein to users 110 having a relationship with one of the entities associated with the medical services or medical insurance. For example, the system 100 may be implemented by an insurance company 118, who maintains the server 102. In other embodiments, the server 102 may be configured to deal with users 110 associated with at least one of a set of such entities.

For example, one user may be insured by insurance company A while another user is insured by insurance company B. Both insurance companies may subscribe to a service provided using the contemplated system 100, implemented using a server 102 and offered as software-as-a-service (SAAS) by another party. As an option, users 110 of the system 100 may be presented with different options (e.g. payment plans, financing options, etc.) based upon which entity through whom they have access to the system 100. In still other embodiments, including the non-limiting example shown in FIG. 1, the system 100 may be implemented, and its benefits provided to users 110, without direct control or sponsorship of any of these entities.

As shown, the system 100 may also include a database 104. In some embodiments, the database 104 may be localized with (e.g. internal to, etc.) the server 102. In other embodiments, the database 104 may be distinct from the server 102. In still other embodiments, the database 104 may be remote to the server 102 (e.g. executed in a cloud environment, etc.). The database 104 may be use to store various information used by the system 100, including but not limited to user profiles and preferences, bills, explanation of benefits, financial records, payment methods, payment histories, biographical information, and the like. The database 104 may be implemented in any architecture known in the art, such as SQL, NoSQL, and the like.

Users 110 interact with the server 102 through a user client device 106 (e.g. phone, tablet, laptop computer, desktop computer, etc.). According to various embodiments, the user-server interaction may be accomplished through various interfaces, including but not limited to, a web portal, a specialized app or application, and the like. In some embodiments, a user 110 may interact with the server 102 by interfacing with a secondary network operating over network 126 or some other network. For example, in one embodiment, a user 110 may interact with the server 102 through a chat bot operating within a social network or through text messaging on a cellular network. In some embodiments, interactions through secondary networks may be limited in nature due to security and privacy regulations surrounding health records. As a specific example, in some embodiments, the system 100 is configured to be HIPAA compliant.

In some embodiments, the server 102 may also be configured to interact with one or more additional servers, which may be associated with an employer (e.g. the user's employer through whom they have medical insurance benefits, etc.), a provider 116 (e.g. hospital, doctor, ambulance company, pharmacy, testing center, etc.), and/or an insurance company 118. In other embodiments, the server 102 may also communicate with third party servers 115 to directly retrieve information specific to the user (e.g. bills, explanation of benefits, remaining deductible, etc.), retrieve general information (e.g. coding schemes, policy limits, coverage explanation, etc.), verify information provided by the user (e.g. verification of insurance policy, validation of postal addresses, etc.), make payments (e.g. interact with payment processing servers, etc.), and the like. Specific interactions with a insurer server 114 and a healthcare provider server 112 will be discussed in greater detail with respect to FIG. 4, below.

As a specific example, in some embodiments, the server 102 may be configured to quickly integrate with other parties, such as providers 116 and insurance companies 118, in multiple ways, to facilitate their interaction with the system 100 and provide quick benefit to the users 110. For example, the server 102 may be able to interact with these parties without any disruption to their existing systems and business practices. As will be discussed further below, server 102 may receive scans or photographs of medical documents 108 sent to the user by these parties, and automatically incorporate that information into the system with only minimal effort from the user (e.g. taking a picture, etc.). Additionally, in some embodiments, the server 102 may also interact directly with the electronic health records systems of the providers 116, insurance companies 118, or other third parties. Rather than information flowing from these parties to the user, and then from the user into the system 100, the information may be brought into the system 100 directly from the other party. The server 102 would then inform the user 110 (e.g. push notification, email, etc.). Such a direct integration would be beneficial to the providers 116 and insurers 118, providing quick communication and further ensuring the bills get paid on time.

As shown, in some embodiments, the server 102 may also be communicatively coupled to an agent client 122, through which a human agent 120 may interact with the system 102. In some embodiments, the system 100 has a mechanism for growth; when questions or situations arise that cannot be handled automatically by the server 102, the problem may be escalated to the human agent 120, through their client 122. Once handled by the human agent 120, the server 102 may then incorporate additional capacity, such that a similar situation may be handled automatically in the future. This will be discussed in greater detail with respect to FIG. 4, below.

Figure 2:
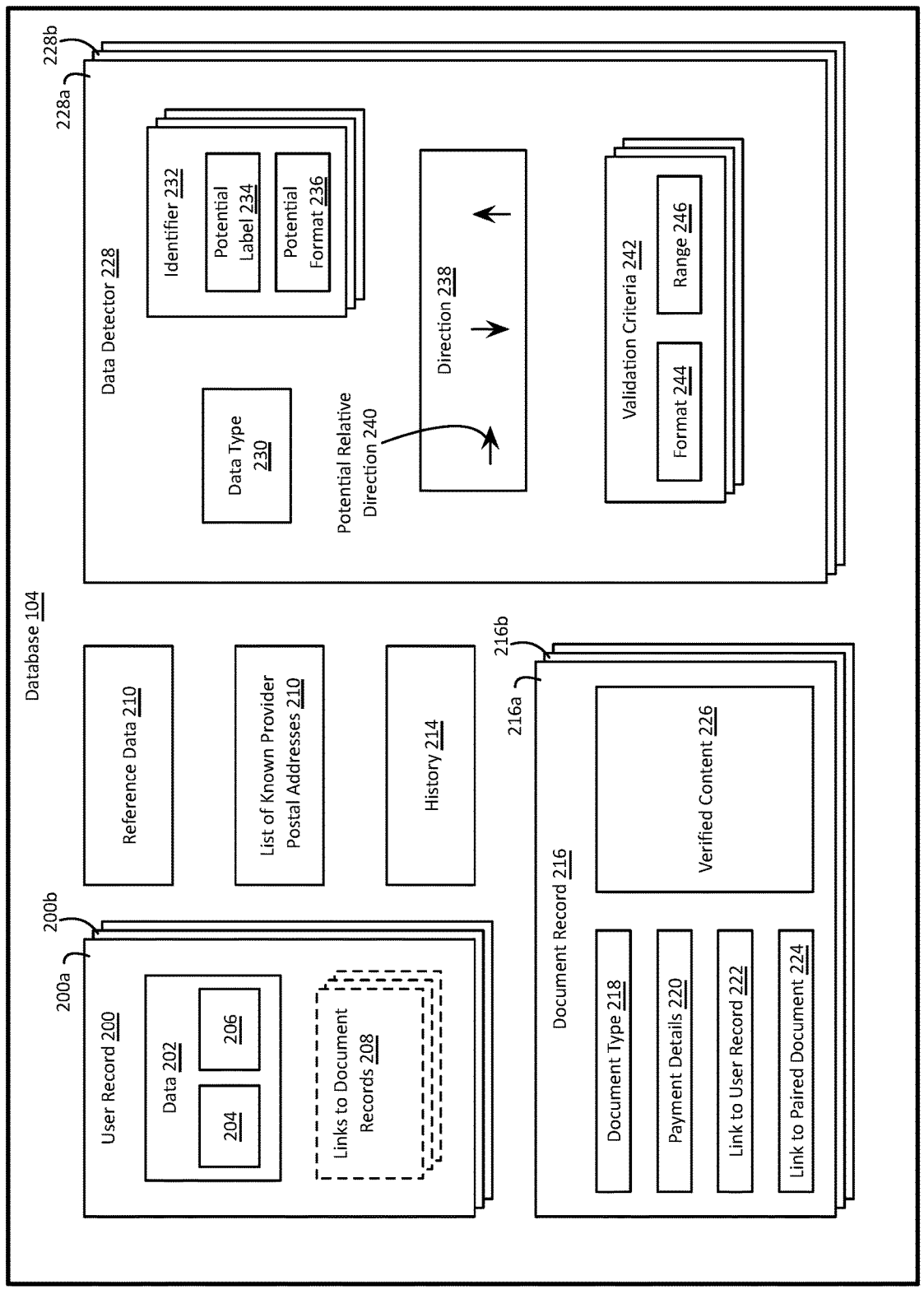
FIG. 2 is a schematic view of the contents of a database belonging to a healthcare document management system.

FIG. 2 is a schematic view of a non-limiting example of a database 104 belonging to a healthcare document management system 100. As shown, the database 104 may be used to store a variety of information, including but not limited to user records 200, document records 216, and information used to ingest documents provided by a user 110. It should be noted that the data objects depicted in FIG. 2 are meant to provide context for a discussion of the various pieces of data that the system 100 works with, and is not meant to be limiting or imply the requirement of a particular structure or storage format. For example, in one embodiment, a user record 200 may comprise links or references to the document records 216 for documents provided by that user, while in another embodiment, the information obtained from a user's documents may be incorporated directly into the user record 200. Those skilled in the art will recognize that there are numerous ways the following information may be organized, stored, and accessed within a database.

As shown, the database 104 comprises a plurality of user records 200. The user record 200 comprises information specific to a user 110 or, in some embodiments, multiple individuals (e.g. information about a family sharing the same healthcare plan, etc.). According to various embodiments, a user record 200 may comprise data 202, and may also point to additional data through one or more links 208 to document records 216. The user data 202 may include, but is not limited to, insurance data 204 (e.g. insurance provider, group number, ID number, deductible, etc.), identifying data 206 (e.g. name, address, date of birth, etc.), payment information, medical history (e.g. previous procedures, events of medical significance, etc.).

According to various embodiments, the database 104 may also comprise reference data 210. As will be discussed in greater detail below with respect to FIG. 4, some embodiments of the system 100 may comprise an integrated help system. In some embodiments, it may take the form of a conversational "chat bot", or virtual agent, with which users can converse and ask questions. In some embodiments, the healthcare document management system 100 contemplated herein not only helps users 110 manage their medical documents, but also provide greater clarity with respect to the healthcare system as a whole, put into the context of that particular user 110 or patient. The reference data 210 may take the form of any expert systems or reference systems known in the art.

The database 104 may also comprise information about various healthcare and insurance providers, to facilitate the recognition of the sources of various documents ingested into the server 102. As will be discussed in greater detail with respect to FIG. 5, in some embodiments, the database 104 may comprise a list 212 of postal addresses that are unique to known healthcare/insurance entities. In other embodiments, additional or other identifying information may be stored and used in similar manner.

As shown, the database 104 also comprises a plurality of document records 216, each comprising data regarding a particular medical document 108. It should be noted that said medical document is not limited to tangible documents ingested into the system, but also electronic, human readable documents (e.g. a PDF of an explanation of benefits, etc.), digital files read for storage in the database 104, and the like.

As shown, according to various embodiments, the document record 216 may comprise a document type 218 (e.g. bill, receipt, explanation of benefits, etc.), payment details 220 (e.g. total amount due, total due date, payment amount due, payment due date, previous payments, etc.), and other verified content 226 (e.g. data ingested from the document 108 that has been verified by the user 110 or some other entity or process, etc.). The document record 216 also comprises a link 222 to the user record 200 of the user 110 that document 108 refers to. The document record 216 may also comprise a link 224 to one or more paired or otherwise related documents (e.g. pairing a bill and an explanation of benefits describing the procedures in the bill, etc.). According to various embodiments, a document record 216 may also comprise tags, flags, events, and/or other metadata that give context to the healthcare that document 108 discusses (e.g. "October 2019 skiing accident", etc.).

The database 104 may also store a plurality of data detectors 228. In the context of the present description and the claims that follow, a data detector 228 is a collection of data that is used to identify and validate particular pieces of information among the text extracted from a document 108.

As shown, each data detector 228 is associated with a data type 230. In the context of the present description and the claims that follow, a data type 230 refers to a specific piece of data (e.g. date of invoice, type of healthcare service rendered, etc.) rather than the species of data (e.g. date, string, etc.).

Each data detector 228 comprises at least one identifier 232, which is a piece of information that can be used to identify an instance of the data type 230 within a document 108. One example of an identifier is a potential label 234, which is a textual indicator identifying a nearby piece of information (e.g. "Payment due", "ID number", etc.). Another example of an identifier is a potential format 236, meaning a patterning of kinds of data (e.g. a dollar sign followed by numbers and a period and two more numbers to indicate a monetary value, etc.).

In some embodiments, a data detector 228 may require the observation of both a label 234 and a format 236. In some embodiments, a data detector 228 may have more than one identifier 232, for information that may be labeled in numerous ways. For example, an identification number could have the labels "ID number", "ID No.", "ID", and the like.

As shown, the data detector 228 also comprises at least one direction 238, meaning one or more potential relative directions 240 where a value may be found, with respect to its identifier. For example, a data detector 228 having an potential label 234 of "Statement Date" may include "right" as a direction 238. Those skilled in the art will recognize that relative direction information may be represented in numerous ways, including verbal (e.g. "right", "up", etc.) and numerical (e.g. Cartesian offset, polar coordinates, etc.).

According to various embodiments, the data detector 228 may also include at least one validation criteria 242, which must be satisfied in order to accept a piece of text content as a value being described by the identifier 232. Examples include, but are not limited to, valid formats 244 (e.g. two decimal places for dollar amounts, etc.) and valid ranges 246 (e.g. date of birth within the last 120 years, etc.).

The database 104 also may comprise one or more history records 214. In the context of the present description and the claims that follow, a history 214 is a collection of observations made during previous document ingestion that are specific to a particular document source (e.g. healthcare provider, insurance provider, bank, etc.) and/or particular document type (e.g. bill, explanation of benefits, check, credit card, insurance card, receipt, etc.). It should be noted that a history 214 is different than a recording of a particular document format. Instead, it provides a preferred ordering for the various potential relative directions 240 and/or identifiers 232 that may be observed by that data detector 228. For example, in one embodiment, if the first medical bill from North Hospital ingested by the server 102 positioned the dollar value for the total amount due to the right of the "total amount due" label, the history 214 for North Hospital bills would place "right" at the front of a list of possible directions for the data detector 228 for that label. The use of histories 214 is advantageous as it permits optimized operation based on previous documents without locking the system 100 into a particular document format, as is done with conventional systems.

Figure 3:
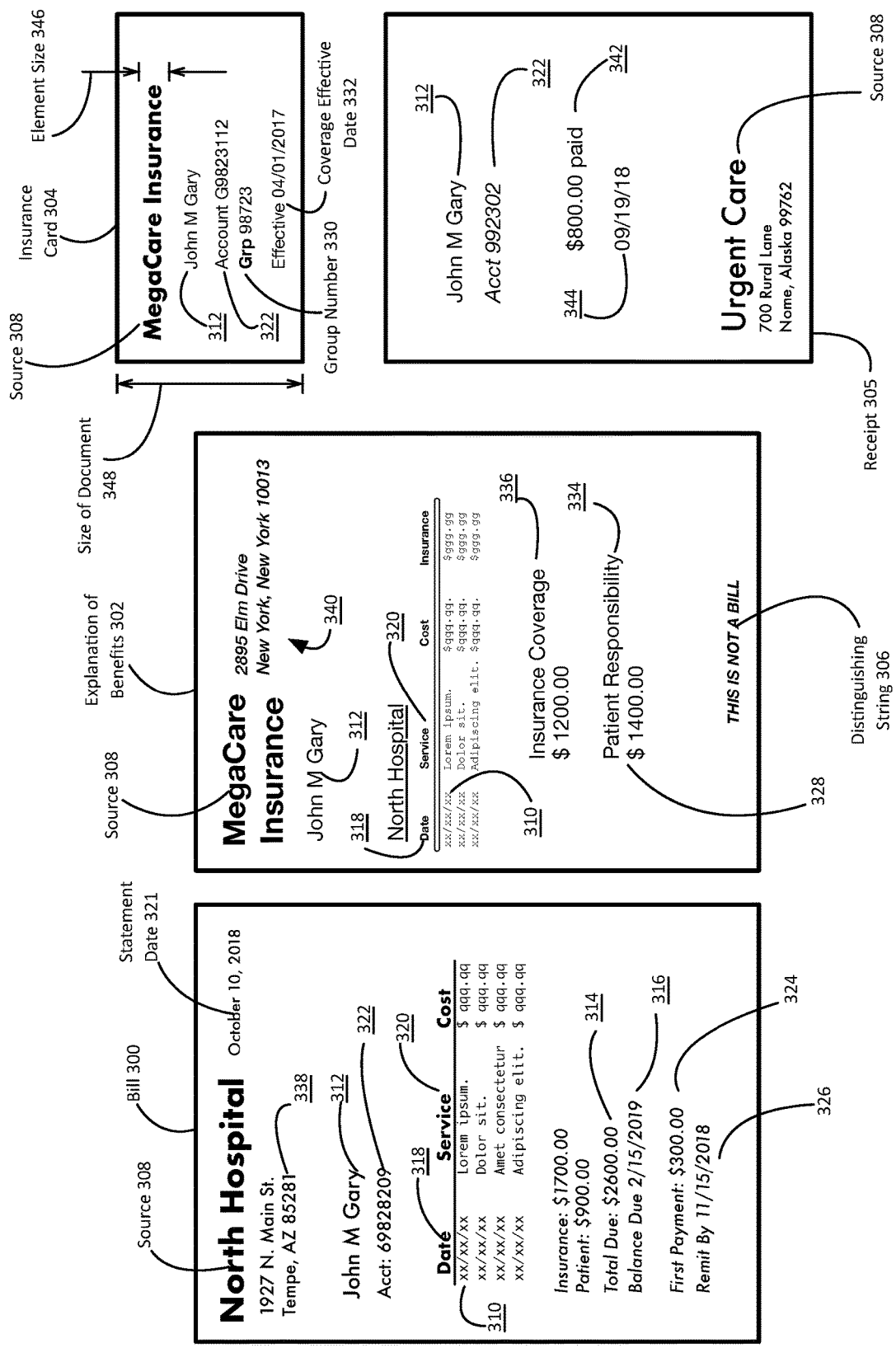
FIG. 3 is a schematic view of four exemplary medical documents.

FIG. 3 is a schematic view of non-limiting examples of four medical documents 108. Specifically, a medical bill 300, an explanation of benefits 302, an insurance card 340, and a receipt 305. As previously mentioned, the healthcare document management system 100 may be configured to ingest, organize, and analyze a variety of documents. In some embodiments, the system 100 may be configured to work with the four types of documents shown in FIG. 3.

As will be discussed in greater detail with respect to FIG. 5, each document had information that is identifiable by position and or a label 334. Until a data detector 228 is employed, each piece of text is a potential descriptor 336.

The system 100 is able to distinguish between two or more document types, according to various embodiments. This is particularly beneficial for document types that may otherwise be confused by a user 110. For example, in some embodiments, the system 100 is able to differentiate between an explanation of benefits and a bill, which sometimes can look very similar. In some embodiments, the system 100 is able to distinguish between document types by searching for a distinguishing string 306, which is a piece of text that is reliably unique to a particular document type. For example, explanation of benefits often have "This is not a bill" printed on them somewhere.

Each document has a source or provider 308 identified, indicating where the document came from or who it is associated with. In some embodiments, bills 300 are paired with explanation of benefits 302 (hereinafter EOB) for convenience and error checking. This pair may be done by searching for a common date 310 shared by both documents (e.g. a date of service, etc.). Many documents also have a postal address 338 for the provider 308, provided in a postal address format 340.

As shown, a bill 300 may include, but is not limited to, patient name 312, a provider 308, a total amount due 314, a balance due date 316, a date of service 318, a service details 320, a statement date 321, and/or an account number 322. Bills 300 may also include a payment amount 324 and a payment due date 326, for bills with an established payment plan.

An EOB 302 is a statement sent by an insurance company that may explain what treatments and/or services were paid for on their behalf, when they occurred, when they were paid, who was paid, a breakdown of the fee, and what the patient is responsible for. The EOB 302 may also include an indication of what claims have been denied, and why, or what adjustments have been made, and why. As shown, in some embodiments, an explanation of benefits 302 may include, but is not limited to, a patient name 312, a provider 308, a date of service 318, a service details 320, and an amount the patient should pay 328.

The processing of EOBs 302 by the system 100 is advantageous to the user 110, even beyond simply tracking financial obligations. EOBs 302 can be very confusing, and important details (e.g. denied claims, etc.) may be lost among all of the information being provided. In some embodiments, the system 100 makes sure the user 110 is aware of what is important, and helps clarify what is confusing, to the benefit of both the user and the other entities.

Some embodiments of the system 100 can process insurance cards 304, which is advantageous as it may further streamline the onboarding process for new users 110. As shown, an insurance card 304 may include, but is not limited to, a patient name 312, a provider 308, an account number 322, a group number 330, and a coverage effective date 332. As will be discussed with respect to FIG. 5, the system 100 may also make note of the size 346 of the document, as well as the size of the text 346 it contains, when differentiating an insurance card 304 from other healthcare documents that may contain similar information.

According to various embodiments, the system 100 may be configured to ingest, organize, and analyze receipts 305 for payments made. As shown, a receipt 305 may include, but is not limited to, patient name 312, a provider 308, a date of service 318, a service details 320, an amount paid 342, and a date paid 344. As will be discussed below, receipts 305 may be used to determine if a payment was made to an out-of-network healthcare provider, and whether or not it can be reimbursed.

Figure 4:
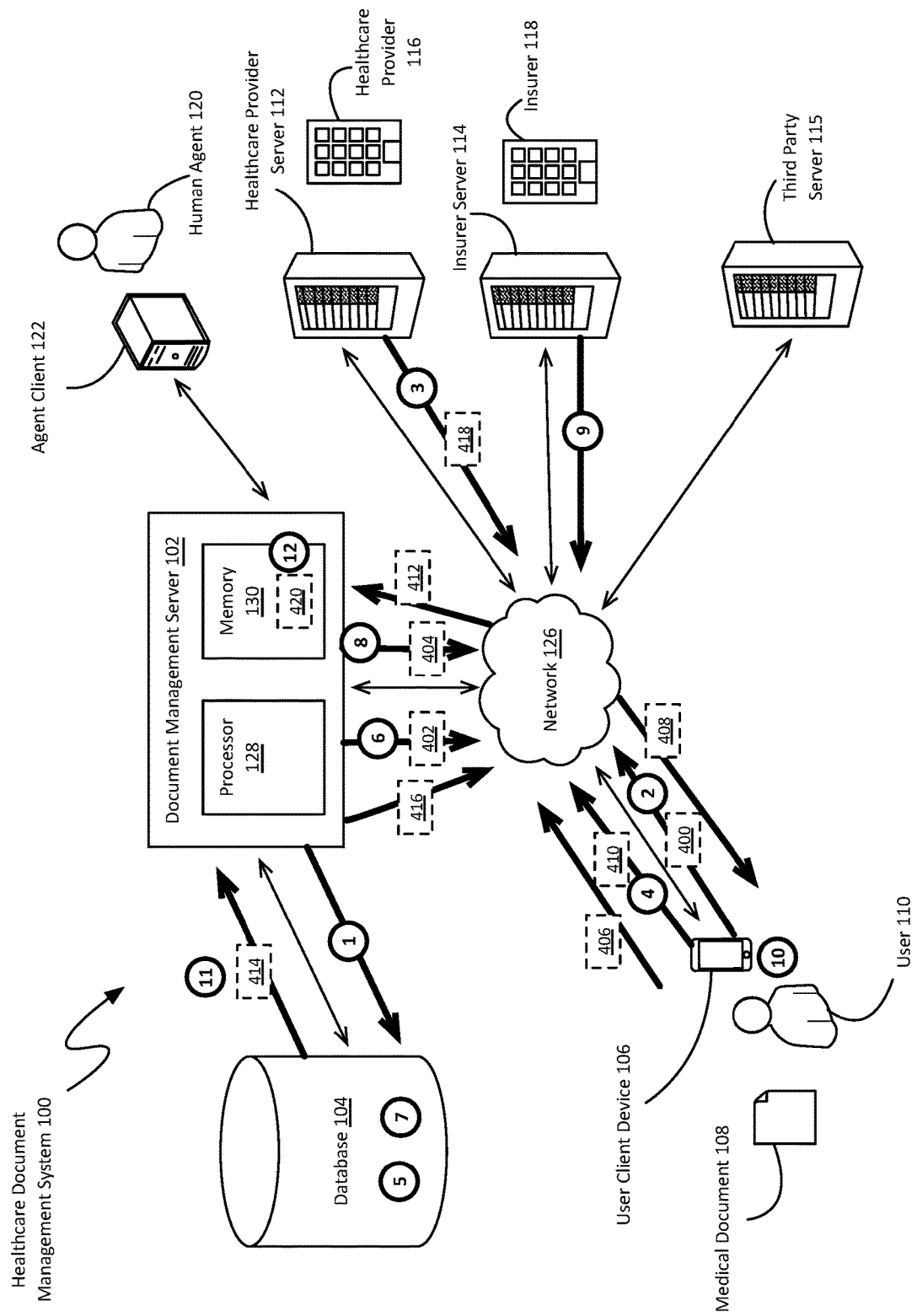
FIG. 4 is a process view of a healthcare document management system.

FIG. 4 is a process view of a non-limiting example of a healthcare document management system 100. According to various embodiments, the server 102 may facilitate the initial information gathering that needs to be performed when creating an account or profile for a new user 110.

According to various embodiments, a user 110 may be given the option of creating their account based upon their email address, or by tying it to an external user authentication system, sometimes provided as part of a social network or other related service or API. Additionally, as is known in the art, at some point in the onboarding process, the user will be presented with a privacy policy and terms of use, to which they must agree before the account may be created.

The creation of a user account continues with the gathering of user information. According to various embodiments, the user information (e.g. name, address, date of birth, etc.) may be gathered, at least in part, through the user client device 106.

In some embodiments, the user may enter information concerning their insurance(s) by simply taking a photo of their insurance card. Using OCR or other machine vision technology, the server 102 will process the images to extract the needed information. The user is then presented with the extracted information, allowing them to confirm the accuracy of the extraction and then move on to scan another insurance card or continue with the onboarding process.

In some embodiments, the system 100 may facilitate the entry of insurance provider information by obtaining the information directly from the insurance provider (e.g. communicating with an insurer server 114 maintained by the insurance provider 118, etc.). For example, a user 110 may provide a minimal amount of information, and the server 102 may utilize existing methods for verifying insurance coverage, as known in the art, to obtain the remaining information. Ultimately, the gathered user information is sent to the server 102, which uses it to create and store a user record 200 in the database 104. See circle '1'.

Once obtained, the provider information, as well as other information associated with the user account, may be used to prepopulate subsequent forms involved in the management of the user's documents. It should be noted that in some embodiments, the user may have the option to skip this information gathering portion of the onboarding process, and enter the information later through a different interface.

In some embodiments, the user may be prompted to enter additional information, if they so choose. This additional information may include, but is not limited to, their employer, their annual income (e.g. to find income-based programs or benefits for reducing medical costs, etc.), gender, date of birth, and the like.

According to various embodiments, documents may be added to the server 102 (e.g. stored in database 104, etc.) using a variety of methods. As previously mentioned, documents may be captured and information extracted by processing images 400 of the document using machine vision or OCR technologies. See circle '2'. Such processing will be discussed in greater detail with respect to FIG. 6, below.

Embodiments making use of a user client device 106 may advantageously make use of a digital camera common to mobile devices. Allowing documents to be added to the system 100 in this way is advantageous in that it provides benefits to the user without requiring any change in procedure or workflows used by the other involved entities (e.g. hospital can continue to send paper bills, etc.).

Another example of a document capture method employed in some embodiments of the system 100 is document upload. While some entities still make use of paper documents, many have moved on to electronic documents. According to various embodiments, the server 102 may allow a user 110 to upload a document through one or more different channels. For example, in one embodiment, the user may be able to forward emails received from providers or insurers directly to the server 102 for processing (e.g. forward email to an address unique to the user, etc.).

In another embodiment, a user may be provided with an interface (e.g. web page, etc.) for selecting a document (e.g. selecting a PDF within a file manager on their client device, etc.) for uploading to the server 102 for processing. In yet another embodiment, the server 102 may allow for the uploading of documents using other authenticated and secure protocols and methods (e.g. FTP, SFTP, etc.) known in the art.

Yet another example of document gathering is the receipt of information directly from an entity, on behalf of the user. See circle '3'. Some embodiments may be configured to communicate directly with other entities on behalf of the user to get bills, explanations of benefits, and other information. In some embodiments, it may be in the form of an external document record 418, which may be formatted for direct storage in the database 104. While requiring a modicum of cooperation between a healthcare entity and the system 100, this direct communication may be advantageous in that it reduces delays in obtaining information (e.g. updates may be pushed by a provider in real time rather than as periodic reports, etc.), as well as the potential for errors in processing traditional physical or digital documents (e.g. optical errors, poor quality, non-standard document formatting, etc.).

Depending on the manner in which it was obtained, after a document has been captured, the user may be prompted to review the information to make sure it is correct. The server 102 may send the content to the user client device 106 for review. The user may be given the option to edit the information as well, and may be informed of information that was expected, but not obtained. Upon user approval, the user client device 106 sends a verification message to the server 102. See circle '4'. Upon verification, the information is stored in the database 104. See circle '5'. In some embodiments, the information obtained from a processed image 400 may be stored, but the image deleted or downgraded in resolution to preserve storage space. In other embodiments, the image 400 may be stored in the database 104, either as part of the document record 216 or as a separate record linked to the document record 216.

After the document has been stored, the system 100 processes the information and updates the user. For example, in some embodiments, the system 100 may determine if a bill or other document is simply a duplicate, or is describing something that has already been recorded after being reported in a different way, by comparing the document record (e.g. first document record 216a, etc.) with the other document records pointed to by the user record 200. Upon determination that a document 108 is a duplicate, the server 102 may send a duplicate document notification 402 to the user client device 106, or otherwise notify the user 110. See circle '6'. Knowing that a bill is a duplicate can come as a relief to a user 110 who may have thought they were faced with yet another large bill from one of many entities, a stress common outside the use of the management systems and methods contemplated herein.

In some embodiments, the server 102, upon creation of a new document record 216a, may determine if there is another document 216b with which it can be paired. For example, a bill and an EOB covering the same matter can be paired. Such a pairing may be made based on common information, such as a date 310. Upon making such a pairing, the correlation may be noted in both document records 216 as a link 224. See circle '7'.

Some embodiments may employ some form of error detection and data corroboration. For example, in one embodiment, the ingestion of a bill or EOB may trigger the server 102 to compare the EOB with bills describing the same treatments or services to determine if there are discrepancies in the reported patient responsibility. There are sometimes discrepancies between what a providers bills and what the insurer says they will pay. For example, a hospital bill may include a $700 charge for a procedure; the EOB may indicate that those procedures are covered at 100% by the users policy, but only shows the insurance company paying the hospital $500, leaving the user owing the hospital $200 in a subsequent bill. Left to manage all of these documents by themselves, it is easy for individuals to miss discrepancies like these. Advantageously, the contemplated system 100 may quickly identify such errors and assist the user in correcting them (e.g. providing contact information for the specific department to handle the error, etc.).

Upon determination that there is a discrepancy between a first document record 216a and a second document record 216b (e.g. reporting different patient responsibilities, etc.), the server 102 may send a billing discrepancy notification 404 to the healthcare provider 116 who is the source of one of the documents associated with the discrepancy, seeking to remedy the discrepancy to the benefit of the user 110. See circle '8'. This notification is sent only after the server 102 has received permission 406 from the user 110 to do so. In some embodiments, the notification 404 may be sent through a channel established for resolving errors and disputes, while in other embodiments, the server 102 may populate the needed information into a human readable document (e.g. email, PDF, etc.) that is sent to the healthcare provider using traditional channels.

Another type of error that often results in patients having to pay more than they should are coding errors. The vast number of medical procedures and treatments require complicated coding systems to allow some form of organization and standardization. However, the boundaries between codes are sometimes not sufficiently sharp, and miscoding is not uncommon. Some embodiments of the system 100 may examine and compare bills and EOBs, and the codes used, to detect if something that should have been covered by insurance was not paid for by the insurance company because it was not correctly coded.

According to various embodiments, the error detection (or in other words, savings discovery) discussed above may be automated using AI and machine learning systems. Analysis of a large data set of documents 108 allows the system 100 to learn how to quickly recognize errors in ways that would be difficult using conventional methods. For example, in some embodiments, the system 100 may identify patterns often found in proximity to certain errors (i.e. a course of treatment that often results in a coding error, etc.). Identifying these patterns makes errors easier to detect. Upon detection, the system 100 may notify the user 110 of the error and the savings they will receive upon correction. In contrast, conventional error detection systems have narrow focus, are not quick to adapt to new problems, and are associated with much greater overhead than the systems and methods employed by various embodiments contemplated herein.

In some embodiments, the system 100 may be configured to ingest, organize, and analyze receipts 305 for payments made to a healthcare provider. One of the benefits of ingesting receipts 305 is that, according to various embodiments and upon identification of the healthcare provider 308 who rendered the care that was paid for, the system 100 can determine if that provider 308 is out-of-network, with respect to the user's insurance, and if it may be submitted for reimbursement. For example, in one embodiment, the system 100 may reach out to the server 114 of the user's insurer 118, taking advantage of a channel established for automatically determining if a provider is in or out of network (said automation becoming more and more common in the healthcare industry, though lacking any of the intelligence and adaptability of the system 100 contemplated herein.). See circle '9'. As an option, upon determination that the payment is eligible for reimbursement, the system 100 may assist the user 110 in requesting the reimbursement, whether by prepopulating a request form or by automatically making the request on behalf of the user 110, upon receipt of user consent.

While healthcare documents 108 are traditionally organized in context of the parties owed or the date of the service, the system 100 also allows for the organization of these documents with respect to events. In the context of the present description, "event" refers to an incident or other occurrences that resulted in the receipt of some sort of healthcare. An example may be a bad fall while skiing. According to various embodiments, the system 100 may provide to the user 110, through the user client device 106, a way of applying a tag or event to a document, allowing the documents to be filtered by a tag or event.

According to various embodiments, a dashboard or other user-facing interface may also allow access to the documents in a chronological or historical organization, as will be discussed below with respect to FIG. 6. The dashboard may also allow a user 110 to specify or modify various preferences and personal information associated with their account.

Presenting information and options in the context of an event helps clarify an otherwise chaotic collection of obligations to various entities. As a specific example, an event could be a bad fall while skiing, resulting in bills for emergency treatment, surgery, medication, specialists, and rehabilitation. Organizing these documents under that unfortunate event allows the user to better understand the big picture, rather than piecing it together using the limited views provided by each healthcare provider.

According to various embodiments, the server 102 may provide the user 110 with an interface for defining a new event and specifying event details including, but not limited to, an event name, event date, event location, notes, and the like. In some embodiments, an event may also have associated documents that are not medical-related, such as accident reports, police reports, legal documents, and so forth, that some embodiments of the system 100 can ingest.

An ingested document can be associated with a defined event. In some embodiments, the user 110 may be prompted to select an event to add the document 108 to, or to create a new event. As an option, the server 102 may use previously captured documents and information to anticipate the most likely event for the recently captured document, and allow the user to simply confirm, or correct. For example, if a user 110 having entered multiple documents for many different events has only seen a particular physical therapist for the event "Nov. 22, 2018 Car Accident", a newly captured document from that physical therapist's office may be presented with a default event of that car accident.

The system 100 may provide an interface for a user 110 to view all bills or other documents associated with an event, perform actions on those bills (as discussed elsewhere in this disclosure), add documents, and remove documents. In some embodiments, the event context may also include a financial summary of the event, such as total expenses, total owed, remaining debt, insurance coverage, and so forth.

According to various embodiments, the system 100 may organize and present the information it has ingested through interfaces on the user client device 106 placing the information in different contexts. See circle '10'. In some embodiments, the interface may display information as documents, each item being a different document. In other embodiments, the user 110 may have the option of breaking the documents down into procedures and treatments, allowing the user to see how the provider and insurer have dealt with, for example, a leg surgery and related expenses.

A user may have the option of flagging a document due to a problem, such as an error or a lack of clarity. According to various embodiments, flagging a document may cause the server 102 to provide the user 110 with a means for contacting the document provider 308 (e.g. provide a tappable link to call the billing department of the hospital, etc.). In some embodiments, the user 110 may have the option of submitting the flagged bill for escalation through a support system provided outside of the billing entity (e.g. customer support for user's insurer, support system provided by entity operating the server 102, etc.).

According to various embodiments, the system 100, after ingesting various healthcare documents 108 provided by the user 110, may the assist the user 110 in meeting their financial obligations as reflected in the documents. In some embodiments, the server 102 may generate a list 408 of payments due by collecting payment details from each document record 216 linked to the user record 200 that is a bill, and then sending the list 408 to the user client device 106. See circle '10'. The list 408 may indicate to the user 110 what bills are coming due soon, how much is owed, when it is due (or how much it is overdue), and the like.

In some embodiments, the system 100 may send the user 110 reminders or notifications regarding bills coming due soon, overdue payments, and other responsibilities. As an option, the system 100 may also notify the user 110 upon the occurrence of certain milestones, such as paying off a healthcare debt. These notifications may come through the user-facing system interface on the user client device 106, and/or may come through other channels (e.g. text message, email, etc.).

According to various embodiments, in the case of overdue payments, the user 110 may be notified when certain amounts of time have elapsed, and the potential consequences if the bill is not paid soon. As an option, in such a case, the user 110 may also be provided with a number of alternatives for getting current, including a payment plan, as will be discussed further below. In some embodiments, upon ingestion of an explanation of benefits 302, the server 102 may notify the user 110 with an update on their insurance coverage and associated information (e.g. remaining deductible, remaining out-of-pocket limits, etc.), and may alert them to denied or partially covered claims.

When a bill 300 is ingested, and is determined to not be a duplicate, the user 110 may be presented with a number of options for dealing with the bill 300. According to various embodiments, the user 110 may be prompted to either pay the bill now, pay it later (e.g. schedule a time for payment to be sent by the system 100, schedule a time to be prompted to make payment, etc.), or set up or modify a payment plan. The ability to take care of various healthcare expenses owed to a variety of providers, using a single interface, makes an otherwise chaotic exercise both manageable and much less intimidating than conventional payment organization systems that are not as adaptable or scalable as the systems and methods contemplated herein.

The system 100 helps users manage their medical bills by facilitating making payments. A user may specify various forms of payment that they system 100 may use to pay bills on behalf of the user, after user confirmation. These payment methods may include, but are not limited to, health savings accounts (HSA), credit/debit cards (e.g. traditional card number and information, mobile payment such as Apple Pay linked to credit/debit card, etc.), ACH, checking accounts, and the like. As an option, a user may specify a primary payment method. The processing of payments will be discussed further with respect to FIG. 7.

According to various embodiments, the system 100 may use the same technology used to ingest healthcare documents 108 to also assist the user in providing payment methods that the system 100 can use to pay the various healthcare entities. For example, in some embodiments, the system 100 may acquire the necessary information for payments to be made using a credit or debit card, or through ACH or electronic check withdrawal, simply by ingesting an image of the card or check provided by the user client device's camera. As an option, the user 110 may also specify a primary payment method among a plurality of payment methods they have activated within the system 100.

In some embodiments, addition of a bill 300 that is not a duplicate but is from a party that is already billing the user 110 may trigger the system 100 to prompt the user 110 regarding bill consolidation. The user 110 may be given the option of viewing all bills 300 to that party in a single chunk, rather than multiple bills 300 that can feel more overwhelming. As an option, the system 100 may figure out what due date to present to the user 110 so the bill 300 is consolidated and none of the component bills are paid late.

Some embodiments of the system 100 may help the user set up a payment plan with the provider directly through the client interface, per parameters provided by the provider. Other embodiments may simply prompt the user 110 for the details of an existing plan (e.g. amounts, due dates, interest, etc.) to be incorporated as reminders and within status reports provided on the user client device 106.

In some embodiments, the user 110 may be provided with a common set of payment plan options that most providers are willing to accept. For example, monthly payments adding up to the full balance due, with a minimum payment of $25 per month and a maximum term of 12 months.

Upon selecting a payment plan option, the user may be informed that the system 100 will submit the request for this payment plan to the provider 308. The provider is then contacted (e.g. electronically, via a provider API, using a human agent, etc.) and informed that a patient has requested a payment plan. As an option, the provider may be given a website URL where they can either reject the payment plan terms or approve the payment plan terms and receive payment.

In some embodiments, that web interface may also allow the provider to authorize and configure the payment plan terms available to all users 110 that are paying that provider. Aspects of the payment plan that may be configured include but are not limited to the minimum payment amount, the payment plan duration, minimum and/or maximum amount due that qualifies for a payment plan, and the like.

Once the payment plan is approved by the provider, the system 100 may automatically send the monthly payments to the provider using the payment method specified by the user 110 (or may prompt the user 110 to make the payment if automatic payments have not been authorized by the user 110). If the system 100 is unable to contact the provider, the provider does not complete the approval and authorization process in a timely fashion, or the provider rejects the payment plan, the system 100 will notify the user 110 that the payment plan was not approved and that they still owe the full amount billed.

As an option, the server 102 will regularly provide to the user 110 a summary of all of the payment plan payments that have been sent to the provider. The summary and, when applicable, the individual payment documents will include the name and email of the person that authorized the payment plan terms on behalf of the provider.

Medical insurance, in general, can be very confusing, using a lot of terminology that may be foreign to a user 110. Furthermore, the way things are described on medical bills, explanations of benefits, and other documents sometimes seems contradictory or unclear. According to various embodiments, the system 100 may assist a user 110 with their questions by providing easy access to needed support, which may be in the form of a list of answered frequently asked questions, or provide access to customer support or other individuals able to answer questions. By providing easy access to this support, the system 100 lessens the burden placed on insurance companies and medical providers.

In some embodiments, users 110 may be provided support through an automated chat bot. Using natural language processing, the automated chat bot allows users to ask questions and receive relevant answers in a manner that is not intimidating or rigid like conventional automated support systems. The server 102 receives, from the client device 106, a query 412 made by the user using natural language. In some embodiments, the interface may resemble a text messaging conversation, while in other embodiments the user 110 may interact with the bot using voice recognition and text-to-speech technologies. In one embodiment, the user 110 may interact with the chat bot through a voice phone call.

Upon receiving the query 412, the server 102 parses it using natural language processing, identifying the desired data. The reference data 210 in the database 104 is searched for data 414 associated with the parsed query. See circle '11'. The server 102 renders a natural language answer 416 to the query using the data 414 associated with the parsed query. The answer 416 is sent back to the user client device 106.

In cases where the query could not be parsed or an answer could not be found, in some embodiments, the query may be escalated to a human agent 120 through an agent client 122 communicatively coupled to the server 102. As an option, efforts by the human agent 120 to respond to the query may automatically result in the reference data 210 being augmented to better handle that query in the future.

In some embodiments, the server 102 may look to other sources of data when forming the answer 416 to the query 412. For example, in some embodiments, the server 102 may contact a third party server 115 to obtain general information (e.g. information regarding a procedure code, information regarding the coverage of a particular insurance plan, etc.). In some embodiments, the server 102 may draw information from the user record 200 when formulating the answer 416, allowing the system 100 to provide an answer to a user's question that is specific to them and their situation, without requiring them to take a general answer and figure out how to apply it to their particular situation, as done in conventional automated support systems.

In some embodiments, the methods discussed thus far may be used as a stepping stone toward automation with artificial intelligence or machine learning. Conventional document management and classification system that use machine learning or artificial intelligence can be effective, but at the cost of painstaking, human-driven training and model refinement. Contemplated herein is a system 100 that not only performs better than conventional systems, it is able to train its own replacement.

According to various embodiments, a machine learning model 420 may be trained to correlate text elements (see text elements 500 of FIG. 5) with data detectors 228 they have been associated with by the server 102. See circle '12'. Periodically, as this model 420 continues to train as the server 102 ingests more documents, the server 102 determines if the machine learning model performs better than one or more of the data detectors 228 being modeled. If the model performs better, the server 102 will automatically employ the machine learning model 420 in place of the one or more data detectors, once they fall behind in performance.

Figure 5:
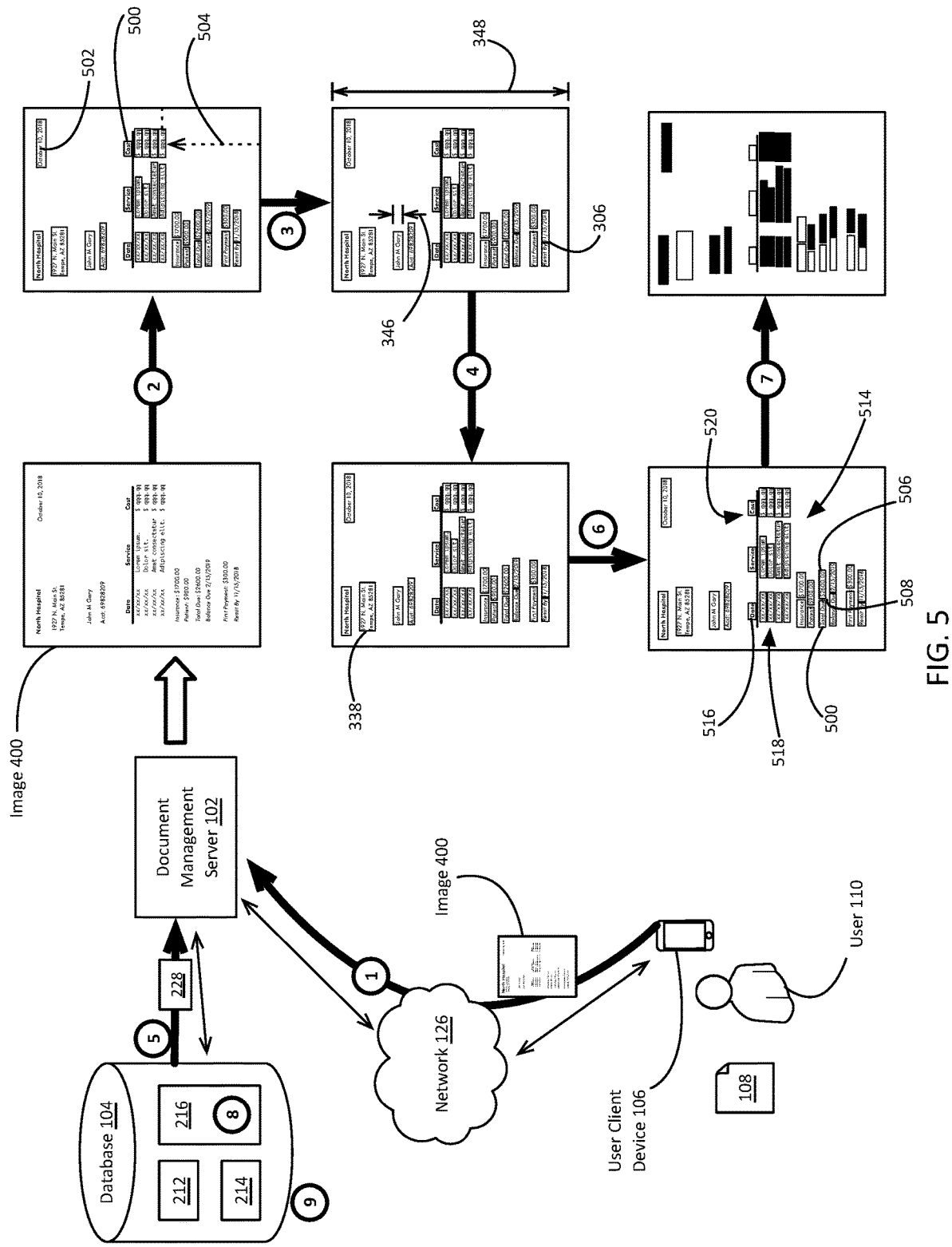
FIG. 5 is a schematic flow of a method for format-agnostic medical document ingestion by a healthcare document management system.

FIG. 5 is a schematic flow for a non-limiting example of format-agnostic medical document ingestion using a healthcare document management system 100. Format-agnostic automated document ingestion provides an advantage over conventional, rigid format based systems or non-scalable, expensive manual systems. Being format-agnostic allows the system 100 to quickly incorporate documents from previously unknown providers or in previously unknown formats, which is time consuming and costly for conventional systems. This also allows the system 100 to work with healthcare providers with great efficiency, without requiring them to make any changes to the way they communicate with patients.

It should be noted that this process is intended for ingesting documents that were intended for human consumption. Documents or files that are computer formatted (e.g. data provided as arrays and matrices, some data structure having indisputable relationships between entries rather than contextual relationships on a two dimensional surface, etc.) may be ingested using much more streamlined methods that may include some form of validation and label/format normalization.

First, the system receives an image 400 of a document 108. See circle '1'. The image 400 may be a digital photograph of the document 108 captured with the user client device 106, or it may be an electronic version of a human-formatted document (e.g. a PDF of an explanation of benefits, etc.), or some other visual format.

Next, the image 400 is converted into a plurality of text elements 500 using optical character recognition or machine vision to identify what is text. See circle '2'. Characters are grouped together as words and sentences using various attributes that may include, but are not limited to, kerning, spacing, alignment, font, and the like. These groupings are turned into individual text elements 500.

In the context of the present description and the claims that follow, a text element 500 is a data object that comprises a content 502 (e.g. the characters, etc.) and an absolute position 504 of that content within the document (e.g. Cartesian coordinates+page number, etc.). In some embodiments, each text element 500 may also include a size of the text, or other visual attributes.

According to various embodiments, the system 100 determines what type of document 108 is being ingested. See circle '3'. In some embodiments, the document type may be provided by the user 106 when they capture an image of the document (e.g. indicating it is a receipt, etc.). In other embodiments, the system 100 may automatically differentiate between two or more possible document types using various methods.

In some embodiments, the system 100 may determine if the document 108 is a bill 300 or an explanation of benefits 302, two document types that are easy for user's to confuse. According to various embodiments, such a determination may be made by searching the content 502 of each text element 500 in the image 400 for at least one distinguishing string 306 that is reliably unique to one particular document type. As a specific example, many EOBs include the words "This is not a bill"; searching for that content 502 may allow the system 100 to determine if the image 400 is of an EOB or not.

In some embodiments, the system 100 may determine what kind of document 108 is being ingested using structural features. For example, in one embodiment, the system 100 may use the actual size of the document 108 to differentiate between an insurance card 304 and some other insurance document that may have very similar information. This determination may be made by comparing the size 346 of the text elements 500 with the relative size 348 of the document 108 in the image 400, allowing the system to conclude if the image is of a card or a letter sized document. Other document types may be determined using visual features that are specific and common to that type (e.g. the particular OCR font used to print the serial number along the bottom left corner of a check, etc.).

Next, the system 100 determines the identity 308 of the healthcare provider (e.g. hospital, lab, insurance company, etc.) that created the document. Some embodiments approach this task using postal addresses, which have a predictable format and are relatively easy to identify.

First, each element 500 is examined to determine if it contains a postal address 338. See circle '4'. After locating an address, it is placed in a uniform postal address format 340 to facilitate comparison with a list 212 of addresses unique to known providers. If the address matches an entry on the list, the provider has been identified. If none of the addresses found in the image are on the list 212, then the system 100 examines the elements that are closest to the found addresses, seeking the provider name. The name may be identified using various methods, including but not limited to comparison with a list of potential providers, a comparison of size and/or formatting of an element closest to the address with the majority of the other elements (e.g. provider name is likely to be visually distinct, etc.), and the like.

Once the document source (i.e. provider 308) has been identified, a plurality of data detectors 228 may be retrieved from the database 104. See circle '5'. The data detectors 228 are selected based on the data types that are anticipated to be in the document, and may be chosen based, at least in part, on the document type (e.g. a first plurality of data detectors 228a may be chosen for an explanation of benefits and a second plurality of data detectors 228b may be chosen for an insurance card, etc.).

In some embodiments, a history 214 specific to that provider 308 (or source) may also be retrieved from the database. Using the history 214, one or more data detectors 228 may be configured, which includes but is not limited to changing the order of the various identifiers 232 and/or directions 238 to reflect the previous observations, as was discussed above.

Once the data detectors 228 have been retrieved and configured, the content of interest may be ingested. In some embodiments, the system 100 may begin with the ingestion of any tables 514 in the document. See circle '6'.

According to various embodiments, a table 514 is identified by calculating, for each element 500, a relative position of at least one neighboring text element 506 using the absolute positions recorded for each element 500. Using these relative positions, elements that are arranged in rows and columns will be apparent.

Next, a header 516 is located, the header 516 being a row 518 or column 520 that contains labeling information for a portion of the table 514. The header 516 may be located by comparing the content of the potential table entries along the borders with the content in the center, according to some embodiments.

Once a potential header 516 is located, it may be confirmed by validating the content of at least one element in the row or column represented by the header element. For example, if the potential header element has the content "Cost", validation may determine if the elements represented by that header element conform to the validation criteria 242 of the data detector 228 for that particular "cost".

Upon validation of the header and the data it represents, the remaining validated elements 500 of the table 514 are associated with the various data detectors 228 that are appropriate for that particular data type (e.g. the detectors 228 used to identify and validate the header elements, etc.).

Next, the remaining elements 500 (i.e. the elements that are not in any tables 514) are examined by first identifying potential descriptor 336 (i.e. a potential label 334) by comparing the element content with various data detectors. Upon finding a potential descriptor 336, it is determined if the element pointed to by one of the at least one direction 238 of the data detector 228 used to identify the potential descriptor 336 meets the validation criteria 242 of the data detector 228. See circle '7'. The validated text elements 500 are then associated with the various appropriate data detectors 228, meaning their content is noted to be of the data type represented by that data detector used to validate.

Next, the content 502 of the validated text elements 500 are stored in the database 104, organized into a document record 216 according to the associations made with the data detectors 228. See circle '8'. Finally, for each data detector 228 that matched, the history 214 associated with the source (i.e. provider 308) is updated according to which identifier 232 and/or direction 238 matched the most text elements of that data type 230 in the document 108. See circle '9'. This advantageously allows the system 100 to continue to operate with efficiency and agility, able to adapt to a change in document format from that provider 308 after a single ingestion, without being stymied by the new formatting like most conventional systems.

Figure 6:
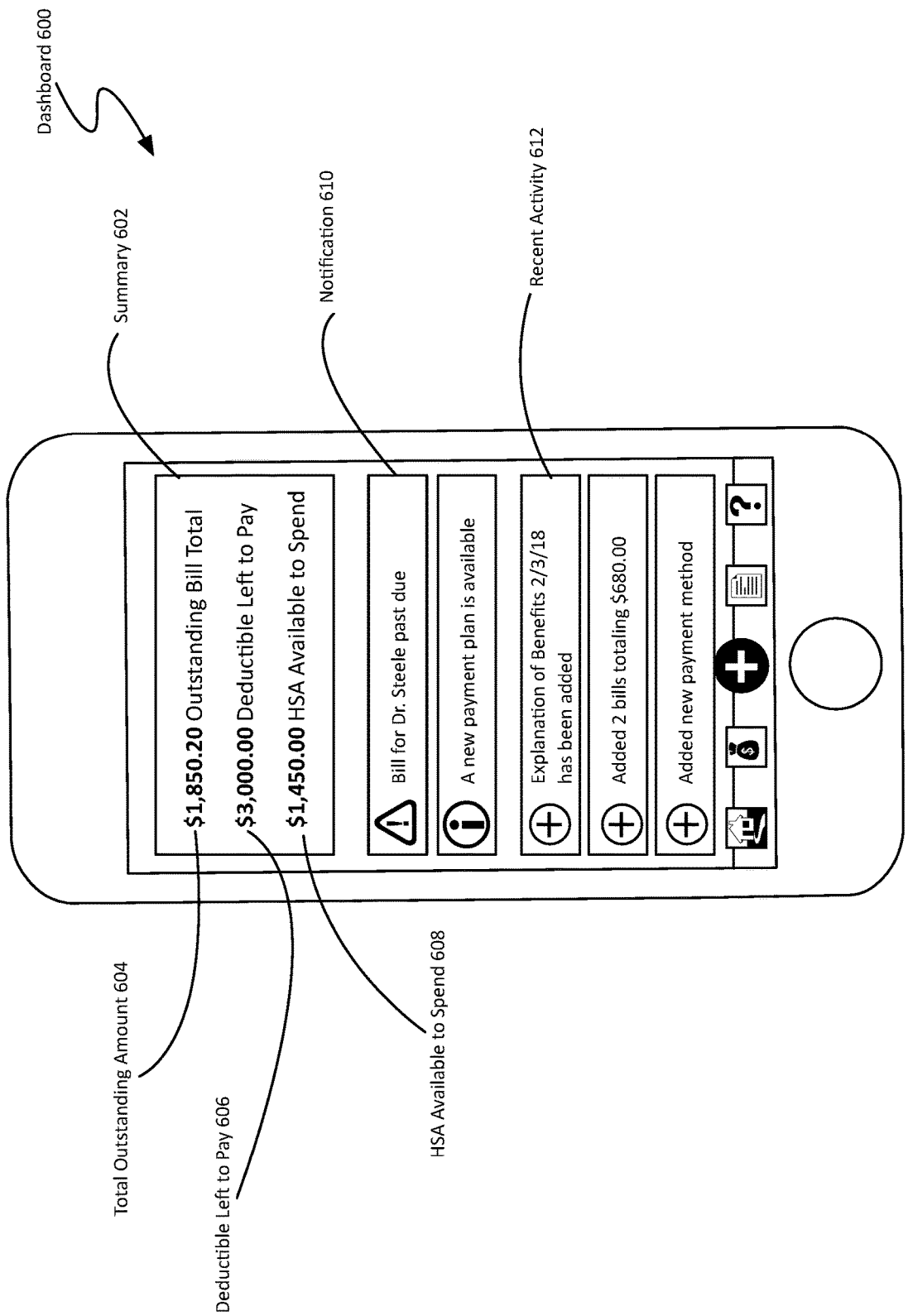
FIG. 6 is a GUI view of an exemplary dashboard on a user client device.

FIG. 6 is a GUI view of an non-limiting example of a dashboard 600 interface for a user client device 106. According to various embodiments, the dashboard 600 may provide a quick summary of the user's various medical events, notification of upcoming or past due bills, and overall financial status, as well as quick access to often used functionality.

As mentioned above, various embodiments of the system 100 may be configured to allow a user to manage the medical bills and insurance coverage for multiple people, such as a family. In some embodiments, the management of a group of people may be performed through a specially designed interface. In other embodiments, management of bills for multiple people may be performed using the single user interface, where the managing user (e.g. parent, etc.) is able to switch between user profiles to see the matters for a specific individual.

As shown, the dashboard 600 provides a summary 602 at the top. Different parts of the summary include the total outstanding amount 604, the insurance deductible left to pay 606, and the HSA account available to spend 608. In other embodiments, the summary 602 may include, but is not limited to, payment/debt (e.g. payment progress, total outstanding debt, number of bills due/paid, money saved to date by using the system 100, etc.), insurance (e.g. deductible left to pay, total deductible, total spent out-of-pocket, etc.), and health savings account (e.g. amount available to spend, amount spent, maximum allowed contribution, etc.). As information is received, either from the user 110 or from various providers 308 and other parties, the values on the dashboard 600 may be automatically updated to provide the most current status to the user 110. It should be noted that other embodiments may organize this information differently, include additional information, or provide less information in the summary 602.

The dashboard 600 may also include notifications 610. Notifications 610 may include, but are not limited to, upcoming bills, past due bills, responses from support inquiries, detected errors, coverage denials, and the like. Particularly urgent notifications 610 may be displayed in a distinct style, as is known in the art. In some embodiments, the notifications 610 may be functional, meaning that interacting with the notification 610 takes the user 110 to an interface where they make take action on said notification 610 (e.g. make/schedule a payment, etc.).

The dashboard 600 may also include a summary of recent activity 612, such as the addition and processing of new documents/payment methods/insurers, the payment of bills, and so forth.

According to various embodiments, the system 100 may assist the user in reducing medical costs. A portion of the savings may be used for the operation of the system 100, with the remained passed on to the user, allowing the user to benefit from the system 100 without having to pay for it.

Examples of how the system 100 may help the user save include, but are not limited to, making it easy to contact a provider to ask for a reduced bill (e.g. click to call, email link, etc.), finding nearby follow-up treatment at a more affordable provider (e.g. using user location data and treatment information from bills and EOBs combined with directory data and medical treatment databases from third parties, etc.), and finding savings programs the user is eligible for (e.g. income based, etc.). In some embodiments, changes in availability of savings options may be indicated to the user via the dashboard 600. For example, if a new potential savings option becomes available, the dashboard 600 may indicate the change to the user.

Figure 7:
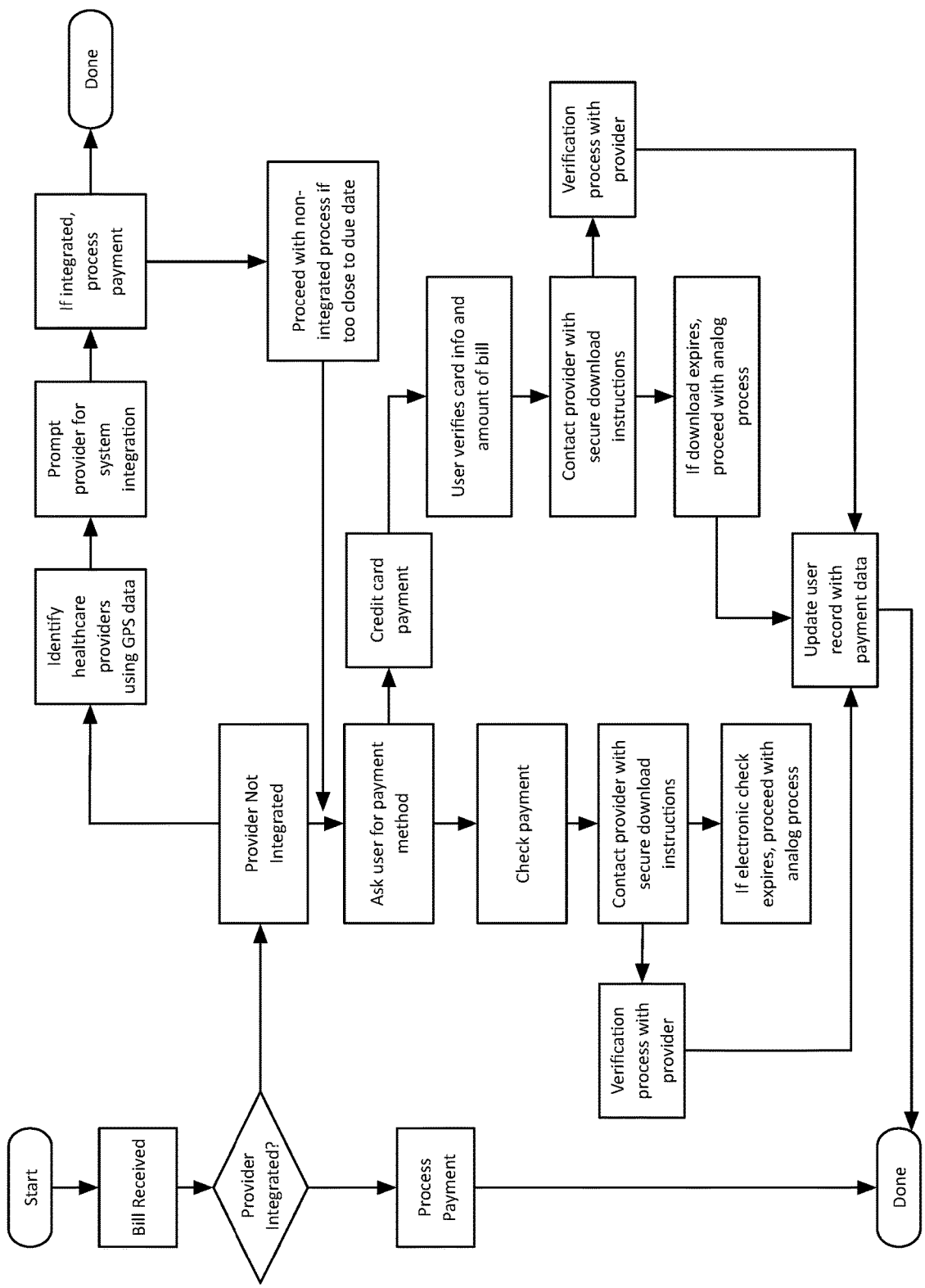
FIG. 7 is an application control flow chart of a method for facilitating payment of healthcare expenses.

FIG. 7 is an application control flow chart of a non-limiting example of a method for facilitating payment through a healthcare document management system 100. One of the biggest benefits provided by the system 100 is the ability to cooperate with various providers and insurance companies in a variety of ways, including ways that do not require any change on their part. As shown in FIG. 7, the payment of a bill 300 begins with a determination of whether the provider or recipient of the funds is integrated within they system 100. If they are integrated with the system 100, payment can be sent directly to them (e.g. paid directly into the providers bank account, etc.). As a specific example, payment may be accomplished through the API of an online payment management service such as Stripe.

Being integrated with the system 100 provides the advantages of fast turn around time on bill payment. If it is determined that they have not been integrated into the system 100, then according to various embodiments that provider may be prompted with an opportunity to integrate, and failing that integration, an out-of-system (i.e. non-integrated) process may be initiated.

FIG. 7 further illustrates an onboarding process within a healthcare document management system 100 for non-integrated parties. Contrary to conventional systems, the system 100 is able to cooperate with healthcare parties without requiring them to change the way they operate.

According to various embodiments, a determination that the provider is out-of-system may trigger two processes. In some embodiments, the user 110 is prompted to select a method of payment, such as credit card or check. In either case, the provider is contacted by the system 100 regarding a secure, electronic download of the check or credit card data. In some embodiments, this information may be provided via an email having a secure link to the data. The link may be configured to expire after a predefined period of time has elapsed without the link being visited. If the link expires before the provider retrieves the payment information, the system 100 may automatically trigger the generation of a hard copy of the information to be sent to the provider via mail. If the link is activated, the provider may be required to go through a verification process before the information is sent.

In some embodiments, the determination that a provider is out-of-system may also trigger a secondary effort to onboard the provider. In one embodiment, GPS data may be obtained from devices associated with the user 110 to identify providers that they have visited. The identified providers may be targeted by a sales team (e.g. team associated with system 100, team associated with third party payment processing service, etc.) who endeavor to onboard the provider. If the provider has not been on boarded within a certain amount of time (e.g. 1 week, etc.) before the bill is due, the system 100 may proceed with the out-of-system payment process, as shown.

Figure 8:
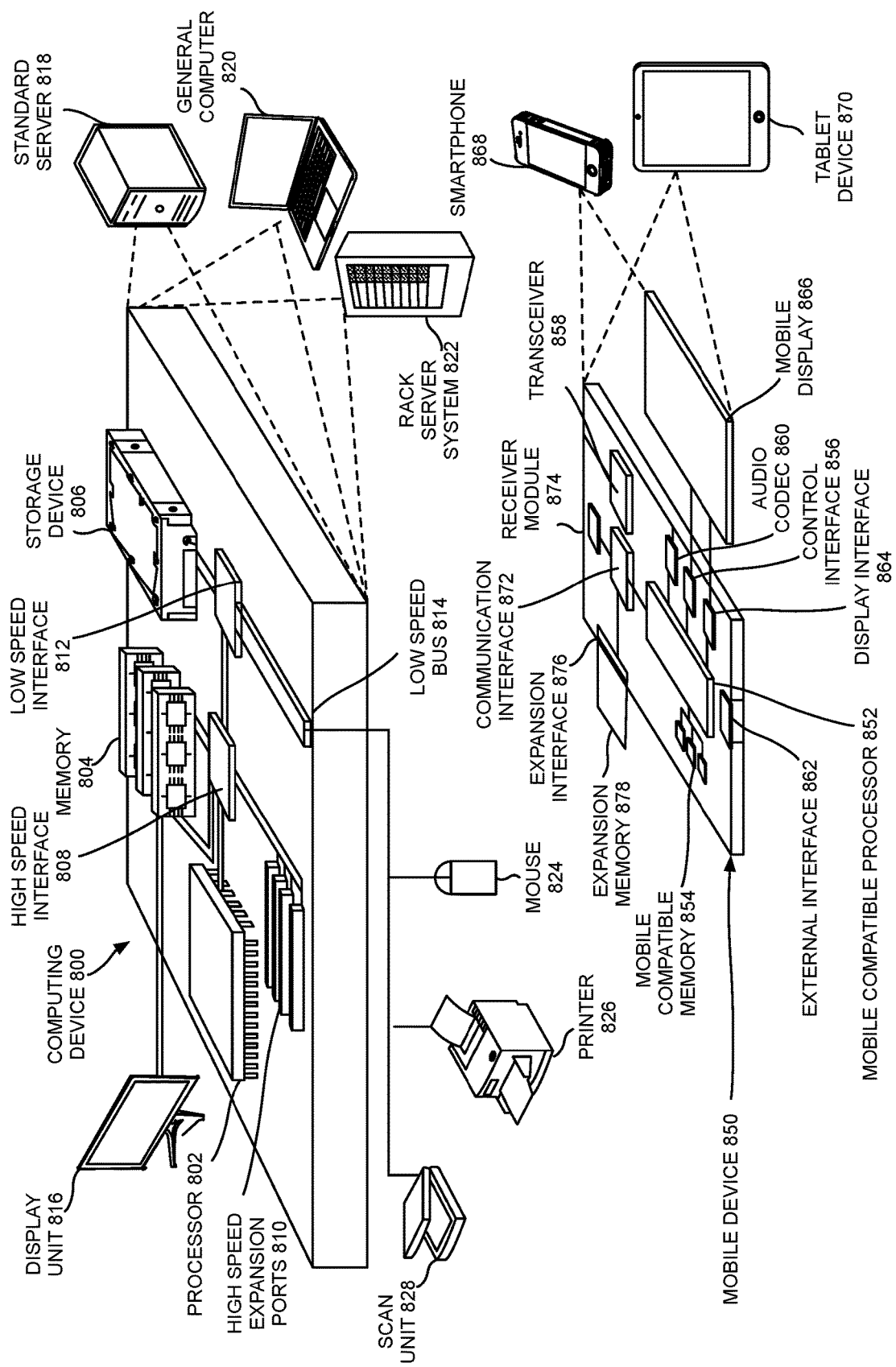
FIG. 8 is a schematic view of a specific computing device that can be used to implement the methods and systems disclosed herein.

FIG. 8 is a schematic diagram of specific computing device 800 and a specific mobile computing device 850 that can be used to perform and/or implement any of the embodiments disclosed herein. In one or more embodiments, document management server 102, healthcare provider server 112, insurer server 114, database 104, agent client 112, and/or user client device 106 of FIG. 1 may be the specific computing device 800. Furthermore, in one or more embodiments, agent client 112, and/or user client device 106 of FIG. 1 may be the specific mobile computing device 850.

The specific computing device 800 may represent various forms of digital computers, such as laptops, desktops, workstations, personal digital assistants, servers, blade servers, mainframes, and/or other appropriate computers. The specific mobile computing device 850 may represent various forms of mobile devices, such as smartphones, camera phones, personal digital assistants, cellular telephones, and other similar mobile devices. The components shown here, their connections, couples, and relationships, and their functions, are meant to be exemplary only, and are not meant to limit the embodiments described and/or claimed, according to one embodiment.

The specific computing device 800 may include a processor 802, a memory 804, a storage device 806, a high speed interface 808 coupled to the memory 804 and a plurality of high speed expansion ports 810, and a low speed interface 812 coupled to a low speed bus 814 and a storage device 806. In one embodiment, each of the components heretofore may be inter-coupled using various buses, and may be mounted on a common motherboard and/or in other manners as appropriate. The processor 802 may process instructions for execution in the specific computing device 800, including instructions stored in the memory 804 and/or on the storage device 806 to display a graphical information for a GUI on an external input/output device, such as a display unit 816 coupled to the high speed interface 808, according to one embodiment.

In other embodiments, multiple processors and/or multiple buses may be used, as appropriate, along with multiple memories and/or types of memory. Also, a plurality of specific computing device 800 may be coupled with, with each device providing portions of the necessary operations (e.g., as a server bank, a group of blade servers, and/or a multi-processor system).

The memory 804 may be coupled to the specific computing device 800. In one embodiment, the memory 804 may be a volatile memory. In another embodiment, the memory 804 may be a non-volatile memory. The memory 804 may also be another form of computer-readable medium, such as a magnetic and/or an optical disk. The storage device 806 may be capable of providing mass storage for the specific computing device 800. In one embodiment, the storage device 806 may be includes a floppy disk device, a hard disk device, an optical disk device, a tape device, a flash memory and/or other similar solid state memory device. In another embodiment, the storage device 806 may be an array of the devices in a computer-readable medium previously mentioned heretofore, computer-readable medium, such as, and/or an array of devices, including devices in a storage area network and/or other configurations.

A computer program may be comprised of instructions that, when executed, perform one or more methods, such as those described above. The instructions may be stored in the memory 804, the storage device 806, a memory coupled to the processor 802, and/or a propagated signal.

The high speed interface 808 may manage bandwidth-intensive operations for the specific computing device 800, while the low speed interface 812 may manage lower bandwidth-intensive operations. Such allocation of functions is exemplary only. In one embodiment, the high speed interface 808 may be coupled to the memory 804, the display unit 816 (e.g., through a graphics processor and/or an accelerator), and to the plurality of high speed expansion ports 810, which may accept various expansion cards.

In the embodiment, the low speed interface 812 may be coupled to the storage device 806 and the low speed bus 814. The low speed bus 814 may be comprised of a wired and/or wireless communication port (e.g., a Universal Serial Bus ("USB"), a Bluetooth® port, an Ethernet port, and/or a wireless Ethernet port). The low speed bus 814 may also be coupled to the scan unit 828, a printer 826, a keyboard, a mouse 824, and a networking device (e.g., a switch and/or a router) through a network adapter.

The specific computing device 800 may be implemented in a number of different forms, as shown in the figure. In one embodiment, the specific computing device 800 may be implemented as a standard server 818 and/or a group of such servers. In another embodiment, the specific computing device 800 may be implemented as part of a rack server system 822. In yet another embodiment, the specific computing device 800 may be implemented as a general computer 820 such as a laptop or desktop computer. Alternatively, a component from the specific computing device 800 may be combined with another component in a specific mobile computing device 850. In one or more embodiments, an entire system may be made up of a plurality of specific computing device 800 and/or a plurality of specific computing device 800 coupled to a plurality of specific mobile computing device 850.

In one embodiment, the specific mobile computing device 850 may include a mobile compatible processor 852, a mobile compatible memory 854, and an input/output device such as a mobile display 866, a communication interface 872, and a transceiver 858, among other components. The specific mobile computing device 850 may also be provided with a storage device, such as a microdrive or other device, to provide additional storage. In one embodiment, the components indicated heretofore are inter-coupled using various buses, and several of the components may be mounted on a common motherboard.

The mobile compatible processor 852 may execute instructions in the specific mobile computing device 850, including instructions stored in the mobile compatible memory 854. The mobile compatible processor 852 may be implemented as a chipset of chips that include separate and multiple analog and digital processors. The mobile compatible processor 852 may provide, for example, for coordination of the other components of the specific mobile computing device 850, such as control of user interfaces, applications run by the specific mobile computing device 850, and wireless communication by the specific mobile computing device 850.

The mobile compatible processor 852 may communicate with a user through the control interface 856 and the display interface 864 coupled to a mobile display 866. In one embodiment, the mobile display 866 may be a Thin-Film-Transistor Liquid Crystal Display ("TFT LCD"), an Organic Light Emitting Diode ("OLED") display, and another appropriate display technology. The display interface 864 may comprise appropriate circuitry for driving the mobile display 866 to present graphical and other information to a user. The control interface 856 may receive commands from a user and convert them for submission to the mobile compatible processor 852.

In addition, an external interface 862 may be provide in communication with the mobile compatible processor 852, so as to enable near area communication of the specific mobile computing device 850 with other devices. External interface 862 may provide, for example, for wired communication in some embodiments, or for wireless communication in other embodiments, and multiple interfaces may also be used.

The mobile compatible memory 854 may be coupled to the specific mobile computing device 850. The mobile compatible memory 854 may be implemented as a volatile memory and a non-volatile memory. The expansion memory 878 may also be coupled to the specific mobile computing device 850 through the expansion interface 876, which may comprise, for example, a Single In Line Memory Module ("SIMM") card interface. The expansion memory 878 may provide extra storage space for the specific mobile computing device 850, or may also store an application or other information for the specific mobile computing device 850.

Specifically, the expansion memory 878 may comprise instructions to carry out the processes described above. The expansion memory 878 may also comprise secure information. For example, the expansion memory 878 may be provided as a security module for the specific mobile computing device 850, and may be programmed with instructions that permit secure use of the specific mobile computing device 850. In addition, a secure application may be provided on the SIMM card, along with additional information, such as placing identifying information on the SIMM card in a non-hackable manner.

The mobile compatible memory may include a volatile memory (e.g., a flash memory) and a non-volatile memory (e.g., a non-volatile random-access memory ("NVRAM")). In one embodiment, a computer program comprises a set of instructions that, when executed, perform one or more methods. The set of instructions may be stored on the mobile compatible memory 854, the expansion memory 878, a memory coupled to the mobile compatible processor 852, and a propagated signal that may be received, for example, over the transceiver 858 and/or the external interface 862.

The specific mobile computing device 850 may communicate wirelessly through the communication interface 872, which may be comprised of a digital signal processing circuitry. The communication interface 872 may provide for communications using various modes and/or protocols, such as, a Global System for Mobile Communications ("GSM") protocol, a Short Message Service ("SMS") protocol, an Enhanced Messaging System ("EMS") protocol, a Multimedia Messaging Service ("MMS") protocol, a Code Division Multiple Access ("CDMA") protocol, Time Division Multiple Access ("TDMA") protocol, a Personal Digital Cellular ("PDC") protocol, a Wideband Code Division Multiple Access ("WCDMA") protocol, a CDMA2000 protocol, and a General Packet Radio Service ("GPRS") protocol.

Such communication may occur, for example, through the transceiver 858 (e.g., radio-frequency transceiver). In addition, short-range communication may occur, such as using a Bluetooth®, Wi-Fi, and/or other such transceiver. In addition, a GPS ("Global Positioning System") receiver module 874 may provide additional navigation-related and location-related wireless data to the specific mobile computing device 850, which may be used as appropriate by a software application running on the specific mobile computing device 850.

The specific mobile computing device 850 may also communicate audibly using an audio codec 860, which may receive spoken information from a user and convert it to usable digital information. The audio codec 860 may likewise generate audible sound for a user, such as through a speaker (e.g., in a handset smartphone of the specific mobile computing device 850). Such a sound may comprise a sound from a voice telephone call, a recorded sound (e.g., a voice message, a music files, etc.) and may also include a sound generated by an application operating on the specific mobile computing device 850.

The specific mobile computing device 850 may be implemented in a number of different forms, as shown in the figure. In one embodiment, the specific mobile computing device 850 may be implemented as a smartphone 868. In another embodiment, the specific mobile computing device 850 may be implemented as a personal digital assistant ("PDA"). In yet another embodiment, the specific mobile computing device, 850 may be implemented as a tablet device 870.

Various embodiments of the systems and techniques described here can be realized in a digital electronic circuitry, an integrated circuitry, a specially designed application specific integrated circuits ("ASICs"), a piece of computer hardware, a firmware, a software application, and a combination thereof. These various embodiments can include embodiment in one or more computer programs that are executable and/or interpretable on a programmable system including one programmable processor, which may be special or general purpose, coupled to receive data and instructions from, and to transmit data and instructions to, a storage system, one input device, and at least one output device.

These computer programs (also known as programs, software, software applications, and/or code) comprise machine-readable instructions for a programmable processor, and can be implemented in a high-level procedural and/or object-oriented programming language, and/or in assembly/machine language. As used herein, the terms "machine-readable medium" and/or "computer-readable medium" refers to any computer program product, apparatus and/or device (e.g., magnetic discs, optical disks, memory, and/or Programmable Logic Devices ("PLDs")) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here may be implemented on a computing device having a display device (e.g., a cathode ray tube ("CRT") and/or liquid crystal ("LCD") monitor) for displaying information to the user and a keyboard and a mouse by which the user can provide input to the computer. Other kinds of devices can be used to provide for interaction with a user as well; for example, feedback provided to the user can be any form of sensory feedback (e.g., visual feedback, auditory feedback, and/or tactile feedback) and input from the user can be received in any form, including acoustic, speech, and/or tactile input.

The systems and techniques described here may be implemented in a computing system that includes a back end component (e.g., as a data server), a middleware component (e.g., an application server), a front end component (e.g., a client computer having a graphical user interface, and/or a Web browser through which a user can interact with an embodiment of the systems and techniques described here), and a combination thereof. The components of the system may also be coupled through a communication network.

The communication network may include a local area network ("LAN") and a wide area network ("WAN") (e.g., the Internet). The computing system can include a client and a server. In one embodiment, the client and the server are remote from each other and interact through the communication network.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

Where the above examples, embodiments and implementations reference examples, it should be understood by those of ordinary skill in the art that other document management systems and methods could be intermixed or substituted with those provided. In places where the description above refers to particular embodiments of document management systems and method, it should be readily apparent that a number of modifications may be made without departing from the spirit thereof and that these embodiments and implementations may be applied to other to document management technologies as well. Accordingly, the disclosed subject matter is intended to embrace all such alterations, modifications and variations that fall within the spirit and scope of the disclosure and the knowledge of one of ordinary skill in the art.

What is claimed is:

1. A healthcare document management system, comprising:
a document management server communicatively coupled to a database, and further communicatively coupled to a user client device through a network, the document management server configured to:
create a user record associated with a user, using information received, at least in part, from the user client device;
store the user record in the database;
receive from the user client device an image of a medical document;
convert the image of the medical document into a plurality of text elements using optical character recognition, each text element having a content and an absolute position in the document;
determine if a document type of the medical document is one of a bill and an explanation of benefits by searching the content of each text element for at least one distinguishing string, each distinguishing string being unique to one document type;
identify all postal addresses in the medical document by inspecting the content of each text element for a postal address format;
validate each postal address;
place each postal address in a standardized postal address format;
determine a source of the medical document by comparing each identified postal address with a list of postal addresses unique to known sources, wherein the source is one of a healthcare provider and an insurer;
determine a source of the medical document having postal addresses not found on the list by examining text elements neighboring each postal address that does not match a postal address found on the user record;
retrieve a plurality of data detectors from the database based on the document type, each data detector associated with a data type that is anticipated to be in the document, each data detector comprising at least one identifier that is one of a potential label and a potential format, at least one direction describing a potential relative direction of a text element having a label associated with the data detector, and at least one validation criteria, wherein each validation criteria describes one of a valid format and a valid range;
for each data detector, order at least one of the identifiers and the directions according to a history stored in the database and associated with the source;
identify a table within the document by calculating for each text element of the plurality of text elements a relative position of at least one neighboring text element relative to the text element using the absolute position of the text element, and comparing the relative positions of the plurality of text elements;
locate a header for the table by comparing the content of the text elements within the table with the identifiers of the plurality of data detectors and then identifying the data type of the matching text elements, the header being one of a row and a column;
validate, for each identified text element in the header, at least one text element within the other of a row and a column described by the identified text element in the header with the validation criteria of the data detector that identified the identified text element in the header;
associate, for each identified text element in the header, at least one validated text element within the other of the row and the column described by the identified text element in the header with the data detector that identified the identified text element in the header;
identify a potential descriptor by comparing the content of each text element not part of the table with the at least one identifier of at least one data detector;
determine if the text element pointed to by one of the at least one direction of the data detector used to identify the potential descriptor meets the validation criteria of the data detector;
associate the validated text element with the data detector;
send to the user client device, for each text element associated with one data detector of the plurality of data detector, the content of the text element, for verification from the user;
receive a verification message from the user client device;
store the verified content in a first document record in the database, the first document record being linked to the user record;
compare the first document record with records associated with other medical documents linked to the user record;
notify the user through the user client device that the medical document is a duplicate upon determination that the medical record already exists;
pair the first document record, which describes one of an explanation of benefits and a bill, with a second document record which describes the other of an explanation of benefits and a bill, based upon at least a common date;
determine if there is a discrepancy between a patient responsibility according to the first document record and a patient responsibility according to the second document record;
notify the user through the user client device of the discrepancy;
generate and transmit a billing discrepancy notification to a healthcare provider who is the source of one of the bill associated with one of the first document record and the second document record, in response to receipt by the document management server of permission from the user client device;
generate a list of payments due by collecting payment details from each bill described by one of a plurality of document records linked to the user record;
send the list to the user client device; and
update, for each data detector, the history associated with the source, according to which identifier of the at least one identifier and which direction of the at least one direction matched the most text elements of the data type described by the data detector in the document.

2. The system of claim 1, wherein the document management server is further configured to:
determine if the document type of the medical document is an insurance card through at least one of comparing a size of the text elements relative to a size of the medical document and searching the content of each text element for at least one distinguishing string unique to insurance cards;
retrieve a second plurality of data detectors from the database, each data detector associated with a data type that is anticipated to be in the insurance card; and
store the verified content in the user record if the document type is insurance card.

3. The system of claim 1, wherein the document management server is further configured to:
receive, from the user client device, a query made by the user in natural language;
parse the query;
search the database for data associated to the parsed query;
send data associated to the parsed query to the user client device; and
escalate the query to a human agent, in response to a lack of data associated to the parsed query in the database, by sending the query to an agent client communicatively coupled to the document management server;
wherein the data associated to the parsed query is retrieved, in part, from the user record, and is specific to the user.

4. The system of claim 1, wherein the document management server is communicatively coupled to at least one of a healthcare provider server and an insurer server through the network, and wherein the document management server is further configured to receive an external document record directly from one of the healthcare server and the insurer server.

5. A healthcare document management system, comprising:
a document management server communicatively coupled to a database, and further communicatively coupled to a user client device through a network, the document management server configured to:
create a user record associated with a user, using information received, at least in part, from the user client device;
store the user record in the database;
receive from the user client device an image of a medical document;
convert the image of the medical document into a plurality of text elements using optical character recognition, each text element having a content and an absolute position in the document;
identify all postal addresses in the medical document by inspecting the content of each text element for a postal address format;
validate each postal address;
place each postal address in a standardized postal address format;
determine a source of the medical document by comparing each identified postal address with a list of postal addresses unique to known sources, wherein the source is one of a healthcare provider and an insurer;
determine a source of the medical document having postal addresses not found on the list by examining text elements neighboring each postal address that does not match a postal address found on the user record;
retrieve a plurality of data detectors from the database, each data detector associated with a data type that is anticipated to be in the document, each data detector comprising at least one identifier that is one of a potential label and a potential format, at least one direction describing a potential relative direction of a text element having a label associated with the data detector, and at least one validation criteria, wherein each validation criteria describes one of a valid format and a valid range;
identify a potential descriptor by comparing the content of each text element with the at least one identifier of at least one data detector;
determine if the text element pointed to by one of the at least one direction of the data detector used to identify the potential descriptor meets the validation criteria of the data detector;
associate the validated text element with the data detector;
send to the user client device, for each text element associated with one data detector of the plurality of data detector, the content of the text element, for verification from the user;
receive a verification message from the user client device; and
store the verified content in a first document record in the database, the first document record being linked to the user record.

6. The system of claim 5, wherein the document management server is further configured to:
compare the first document record with records associated with other medical documents linked to the user record; and
notify the user through the user client device that the medical document is a duplicate upon determination that the medical record already exists.

7. The system of claim 5, wherein the document management server is further configured to:
determine if a document type of the medical document is one of a bill and an explanation of benefits by searching the content of each text element for at least one distinguishing string, each distinguishing string being unique to one document type; and pair the first document record, which describes one of an explanation of benefits and a bill, with a second document record which describes the other of an explanation of benefits and a bill, based upon at least a common date;

wherein retrieving the plurality of data detectors from the database is based, at least in part, on the document type.

8. The system of claim 7, wherein the document management server is further configured to:

determine if there is a discrepancy between a patient responsibility according to the first document record and a patient responsibility according to the second document record; and notify the user through the user client device of the discrepancy.

9. The system of claim 6, wherein the document management server is further configured to:

determine if the document type of the medical document is an insurance card through at least one of comparing a size of the text elements relative to a size of the medical document and searching the content of each text element for at least one distinguishing string unique to insurance cards;

retrieve a second plurality of data detectors from the database, each data detector associated with a data type that is anticipated to be in the insurance card; and store the verified content in the user record if the document type is insurance card.

10. The system of claim 5, the document management server further configured to:

receive, from the user client device, a query made by the user in natural language;

parse the query;

search the database for data associated to the parsed query;

send data associated to the parsed query to the user client device; and escalate the query to a human agent, in response to a lack of data associated to the parsed query in the database, by sending the query to an agent client communicatively coupled to the document management server.

11. The system of claim 10, wherein the data associated to the parsed query is retrieved, in part, from the user record, and is specific to the user.

12. The system of claim 5, wherein the document management server is further configured to:

for each data detector, order at least one of the identifiers and the directions according to a history stored in the database and associated with the source; and update, for each data detector, the history associated with the source, according to which identifier of the at least one identifier and which direction of the at least one direction matched the most text elements of the data type described by the data detector in the document.

13. The system of claim 5, wherein the document management server is further configured to:

identify a table within the document by calculating for each text element of the plurality of text elements a relative position of at least one neighboring text element relative to the text element using the absolute position of the text element, and comparing the relative positions of the plurality of text elements;

locate a header for the table by comparing the content of the text elements within the table with the identifiers of the plurality of data detectors and then identifying the data type of the matching text elements, the header being one of a row and a column;

validate, for each identified text element in the header, at least one text element within the other of a row and a column described by the identified text element in the header with the validation criteria of the data detector that identified the identified text element in the header; and associate, for each identified text element in the header, at least one validated text element within the other of the row and the column described by the identified text element in the header with the data detector that identified the identified text element in the header.

14. The system of claim 5, wherein the document management server is communicatively coupled to at least one of a healthcare provider server and an insurer server through the network, and wherein the document management server is further configured to receive an external document record directly from one of the healthcare server and the insurer server.

15. A computer-implemented method for healthcare document management, comprising:

creating, with a processor, a user record associated with a user, using information received, at least in part, from a user client device;

receiving, by the processor, from the user client device an image of a medical document;

converting, with the processor, the image of the medical document into a plurality of text elements using optical character recognition, each text element having a content and an absolute position in the document;

identifying, with the processor, all postal addresses in the medical document by inspecting the content of each text element for a postal address format;

determining, with the processor, a source of the medical document by comparing each identified postal address with a list of postal addresses unique to known sources, wherein the source is one of a healthcare provider and an insurer;

determining, with the processor, a source of the medical document having postal addresses not found on the list by examining text elements neighboring each postal address that does not match a postal address found on the user record;

retrieving, with the processor, a plurality of data detectors, each data detector associated with a data type that is anticipated to be in the document, each data detector comprising at least one identifier that is one of a potential label and a potential format, at least one direction describing a potential relative direction of a text element having a label associated with the data detector, and at least one validation criteria, wherein each validation criteria describes one of a valid format and a valid range;

identifying, with the processor, a potential descriptor by comparing the content of each text element with the at least one identifier of at least one data detector;

determining, with the processor, if the text element pointed to by one of the at least one direction of the data detector used to identify the potential descriptor meets the validation criteria of the data detector;

associating, in a memory, the validated text element with the data detector;

sending, with the processor, to the user client device, for each text element associated with one data detector of the plurality of data detector, the content of the text element, for verification from the user;

receiving, by the processor, a verification message from the user client device; and storing, in the memory, the verified content in a first document record, the first document record being linked to the user record.

16. The method of claim 15, further comprising:

determining, with the processor, if a document type of the medical document is one of a bill and an explanation of benefits by searching the content of each text element for at least one distinguishing string, each distinguishing string being unique to one document type;

pairing, in the memory, the first document record, which describes one of an explanation of benefits and a bill, with a second document record which describes the other of an explanation of benefits and a bill, based upon at least a common date;

determining if there is a discrepancy between a patient responsibility according to the first document record and a patient responsibility according to the second document record; and notifying the user through the user client device of the discrepancy.

17. The method of claim 16, further comprising:

determining if the document type of the medical document is an insurance card through at least one of comparing a size of the text elements relative to a size of the medical document and searching the content of each text element for at least one distinguishing string unique to insurance cards;

retrieving a second plurality of data detectors, each data detector associated with a data type that is anticipated to be in the insurance card; and storing the verified content in the user record if the document type is insurance card.

18. The method of claim 15, further comprising:

comparing, with the processor, the first document record with records associated with other medical documents linked to the user record; and notifying, with the processor, the user through the user client device that the medical document is a duplicate upon determination that the medical record already exists.

19. The method of claim 15, further comprising:

for each data detector, ordering at least one of the identifiers and the directions according to a history associated with the source; and updating, for each data detector, the history associated with the source, according to which identifier of the at least one identifier and which direction of the at least one direction matched the most text elements of the data type described by the data detector in the document.

20. The method of claim 15, further comprising:

training a machine learning model correlating text elements with the data detectors with which they have been associated;

determining whether the machine learning model performs better than one or more data detectors; and automatically employing the machine learning model in place of the one or more data detectors once the machine learning model outperforms the one or more data detectors.

* * * * *